United States Patent
Kanter et al.

(10) Patent No.: US 9,931,372 B2
(45) Date of Patent: Apr. 3, 2018

(54) SYNTHETIC APELIN FATTY ACID CONJUGATES WITH IMPROVED HALF-LIFE

(71) Applicant: Novartis AG, Basel (CH)

(72) Inventors: Aaron Kanter, Somerville, MA (US); Aimee Richardson Usera, Winchester, MA (US); Frederic Zecri, Brookline, MA (US)

(73) Assignee: NOVARTIS AG, Basel (CH)

( * ) Notice: Subject to any disclaimer, the term of this patent is extended or adjusted under 35 U.S.C. 154(b) by 67 days.

(21) Appl. No.: 14/996,418

(22) Filed: Jan. 15, 2016

(65) Prior Publication Data

US 2016/0213743 A1    Jul. 28, 2016

Related U.S. Application Data

(60) Provisional application No. 62/107,040, filed on Jan. 23, 2015.

(51) Int. Cl.
*A61K 38/12* (2006.01)
*A61K 47/64* (2017.01)
(Continued)

(52) U.S. Cl.
CPC .............. *A61K 38/12* (2013.01); *A61K 45/06* (2013.01); *A61K 47/542* (2017.08); *A61K 47/60* (2017.08);
(Continued)

(58) Field of Classification Search
None
See application file for complete search history.

(56) References Cited

U.S. PATENT DOCUMENTS

| 2004/0116336 A1 | 6/2004 | Kitada et al. |
| 2011/0305663 A1 | 12/2011 | Gosselin et al. |
| 2014/0275489 A1 | 9/2014 | Stevis et al. |

FOREIGN PATENT DOCUMENTS

| WO | 2011/143208 A1 | 11/2011 |
| WO | 2012/125408 A1 | 9/2012 |

(Continued)

OTHER PUBLICATIONS

Kawahara H. et al.: "Tumor endothelial cell-specific drug delivery system using apelin-conjugated liposomes"; Department of Signal Transduction, Research Institute for Microbial Diseases, Osaka University, Suita, Osaka, Japan; PLoS One (2013), 8(6), e65499.

(Continued)

Primary Examiner — Satyanarayana R Gudibande
Assistant Examiner — Jia-Hai Lee
(74) Attorney, Agent, or Firm — Judith D. Kuntz

(57) ABSTRACT

The invention provides a conjugate, or a pharmaceutically acceptable salt thereof, comprising a synthetic polypeptide of Formula I:

Q-R-P-R-L-C*-H-K-G-P-(Nle)-C*-F    (I)

or a amide or ester thereof; and a fatty acid selected from:

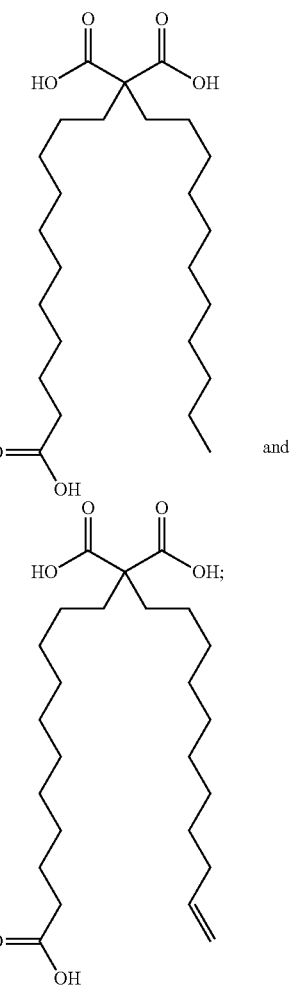

wherein said fatty acid is covalently linked to the N-terminus of the peptide via one of its carboxylic acid functionality, optionally via a polyethylene glycol linker; and wherein the two cysteine amino acids labeled with "*" form a disulfide bond between the thiol functionalities of their side chain. The conjugates are agonist of the APJ receptor. The invention also relates to a method for manufacturing the conjugates of the invention, and its therapeutic uses such as treatment or prevention of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, (Continued)

arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia. The present invention further provides a combination of pharmacologically active agents and a pharmaceutical composition.

16 Claims, 1 Drawing Sheet

(51) Int. Cl.
*A61K 51/04* (2006.01)
*A61K 45/06* (2006.01)
*C07K 14/47* (2006.01)
*A61K 47/60* (2017.01)
*A61K 47/54* (2017.01)
*C07K 7/64* (2006.01)

(52) U.S. Cl.
CPC .......... *A61K 47/64* (2017.08); *A61K 51/0402* (2013.01); *C07K 14/47* (2013.01); *C07K 7/64* (2013.01)

(56) References Cited

FOREIGN PATENT DOCUMENTS

| WO | 2013/111110 A2 | 8/2013 |
| WO | 2014/099984 A1 | 6/2014 |
| WO | 2015/013168 A1 | 1/2015 |
| WO | 2015/013169 A2 | 1/2015 |
| WO | 2015/191781 A2 | 12/2015 |
| WO | 2015/200078 A1 | 12/2015 |
| WO | 2016/102648 A1 | 6/2016 |

OTHER PUBLICATIONS

Jia Z. Q. et al.: "Cardiovascular effects of a PEGylated apelin";Genzyme, a Sanofi Company, Framingham, MA; Peptides, 38(1),181-188.

Mouse plasma exposure profiles of compounds of examples 1 and 4 following subcutaneous dosing
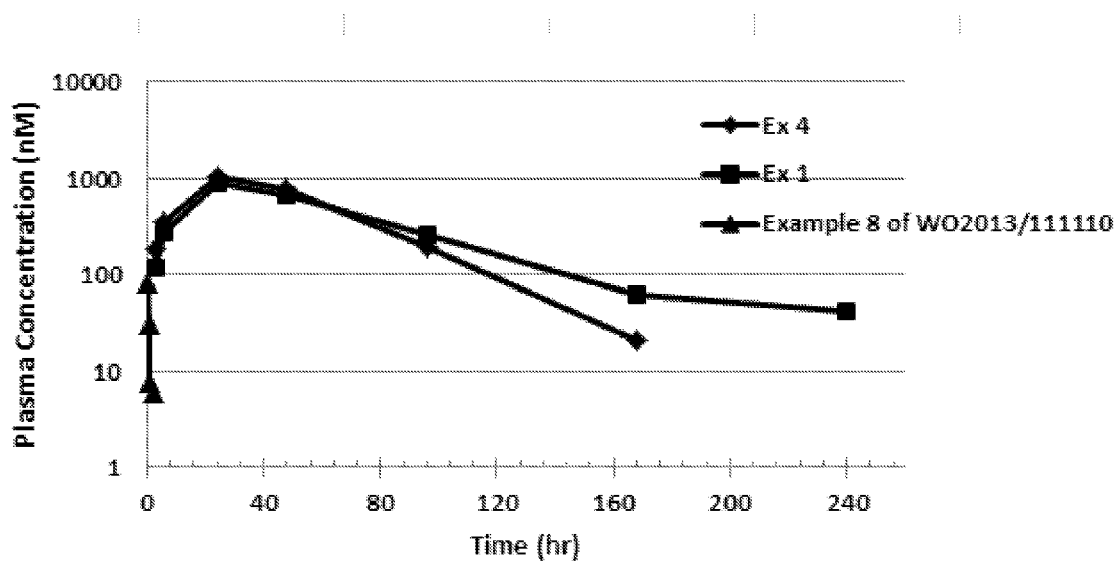

SYNTHETIC APELIN FATTY ACID CONJUGATES WITH IMPROVED HALF-LIFE

This application claims benefit under 35 U.S.C. § 119(e) of U.S. Provisional Application No. 62/107,040, filed Jan. 23, 2015; the content of which is incorporated herein by reference in their entirety.

FIELD OF THE INVENTION

The present invention relates to compositions comprising semi synthetic biologic molecules which are bioconjugates of an APJ agonist polypeptide and a fatty acid moiety. In particular, the bioconjugates of the invention, while retaining APJ agonistic activity, exhibit greater resistance to proteolytic degradation via the action of peptidases as compared to their corresponding naked polypeptide and/or as compared to previously described Apelin bioconjugates. The invention further relates to methods of making said composition and using said compositions as pharmaceutically active agent in the treatment of cardiovascular diseases.

BACKGROUND OF THE INVENTION

The incidence of heart failure in the Western world is approximately 1/100 adults after 65 yrs of age. The most common pathology is a chronic deficit in cardiac contractility and, thereby, cardiac output, i.e., the effective volume of blood expelled by either ventricle of the heart over time. Patients with chronic heart failure can have acute episodes of decompensation, i.e., failure of the heart to maintain adequate blood circulation, where cardiac contractility declines further. There are ~500K hospitalizations per year for "acute decompensated heart failure" (ADHF) in the USA alone.

Current therapies for ADHF include diuretics, vasodilators, and inotropes, which directly increase cardiac contractility. Current intravenous inotropes (dobutamine, dopamine, milrinone, levosimendan) are used in the acute setting, despite their association with adverse events such as arrhythmia and increased long-term mortality. These liabilities have prevented their application in chronic heart failure. Digoxin is an oral inotrope, but is limited by a narrow therapeutic index, increased arrhythmogenic potential and contraindication in renal insufficiency.

A therapy for heart failure that increases cardiac contractility without arrhythmogenic or mortality liabilities is urgently needed for ADHF, but could also address the enormous unmet medical need in chronic heart failure.

Apelin is the endogenous ligand for the previously orphan G-protein-coupled receptor (GPCR), APJ, also referred to as apelin receptor, angiotension-like-1 receptor, angiotension II-like-1 receptor, and the like. The apelin/APJ pathway is widely expressed in the cardiovascular system and apelin has shown major beneficial cardiovascular effects in pre-clinical models. Acute apelin administration in humans causes peripheral and coronary vasodilatation and increases cardiac output (Circulation. 2010; 121:1818-1827). As a result, APJ agonism is emerging as an important therapeutic target for patients with heart failure. Activation of the apelin receptor APJ is thought to increase cardiac contractility and provide cardioprotection, without the liabilities of current therapies. However, the native apelins exhibit a very short half life and duration of action in vivo. The very short half life is a recognized major difficulty with the delivery of such therapeutic endogenous peptides due to rapid serum clearance and proteolytic degradation via the action of peptidases.

One way which has been currently used to overcome this disadvantage is to administer large dosage of therapeutic peptide of interest to the patient so that even if some therapeutic peptide is degraded, enough remains to be therapeutically effective. However, this method is uncomfortable to patients. Since most therapeutic peptides cannot be administered orally, the therapeutic peptide would have to be either constantly infused, frequently infused by intravenous injection or administered frequently by the inconvenient route of subcutaneous injections. The need for frequent administration also results in many potential peptide therapeutics having an unacceptable high projected cost of treatment. The presence of large amounts of degraded peptide may also generate undesired side effects.

Discomfort in administration and high costs are two reasons why most therapeutic peptides with attractive bioactivity profiles may not be developed as drug candidates.

Therefore, one approach to prolong half-life of peptides is to modify the therapeutic peptides in such a way that their degradation is slowed down while still maintaining biological activity. Such synthetically modified polypeptides have been described in U.S. Pat. No. 8,673,848. Another approach includes reducing the rate of clearance by conjugating the peptides to one or more molecules such as fatty acid moieties which may prevent their elimination through kidney. Examples of such fatty acid conjugates have been described in U.S. provisional application No. 62/082,327, in U.S. patent application Ser. No. 14/336,290 and in U.S. patent application Ser. No. 14/336,262.

Such bio-conjugates, however may still be susceptible to protease activity or may no longer be as active as their unconjugated analogs.

There is thus a need for modified therapeutic peptides with increased half-life in order to provide longer duration of action in vivo, while maintaining low toxicity yet retaining the therapeutic advantages of the modified peptides.

BRIEF DESCRIPTION OF THE FIGURE

FIG. 1. represents mouse plasma exposure profiles of compound of Examples 1 and 4 following subcutaneous dosing.

BRIEF DESCRIPTION OF THE INVENTION

This invention is directed to overcoming the problem of peptide degradation in the body by modifying the therapeutic peptide or polypeptide of interest, i.e. APJ agonists.

Therefore the aim of the present invention is to provide novel conjugates or pharmaceutically acceptable salt thereof, comprising a) a peptide having the following formula (I):

a. an APJ agonist peptide having the following Formula (I):

$$Q\text{-}R\text{-}P\text{-}R\text{-}L\text{-}C^*\text{-}H\text{-}K\text{-}G\text{-}P\text{-}(Nle)\text{-}C^*\text{-}F \qquad (I);$$

or an amide or ester thereof,
or a peptide substantially equivalent thereto; wherein the two cysteine amino acids labeled with "*" form a disulfide bond between the thiol functionalities of their side chain; and b. a fatty acid selected from:

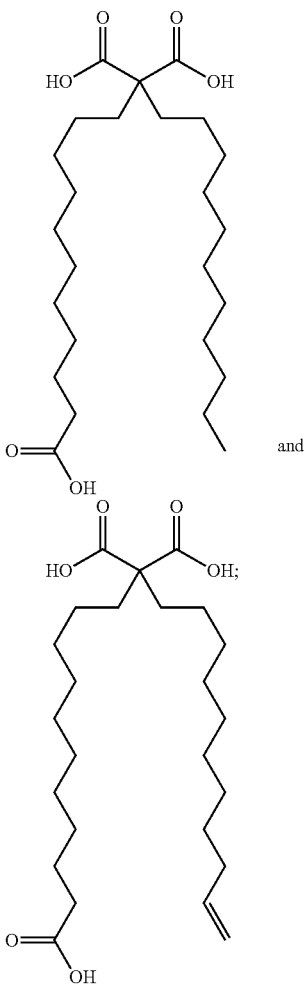

and wherein said fatty acid is covalently linked to the N-terminus of the peptide via one of its carboxylic acid functionality, optionally via a polyethylene glycol linker.

In one embodiment, the conjugates of the invention possess at least one of the following improvements over wild type apelin, and/or over naked (non-conjugated) apelin analogs (e.g. Q-R-P-R-L-C*-H-K-G-P-(Nle)-C*-F) and/or over other previously described apelin conjugates: increased half-life; greater immunity to degradation upon administration and/or upon solubilization; greater agonistic activity at the APJ receptor. The apelin conjugates of this invention are thus particularly useful for the treatment or prevention of cardiovascular diseases such as heart failure, disorders and conditions associated with heart failure, and disorders and conditions responsive to the activation of APJ receptor activity.

Any of the above-listed amino acid residues of Formula I, may be substituted in a conservative fashion, provided the conjugate of the invention still retains functional activity and structural properties (e.g., half-life extension, protection from degradation, conformational constraint). Principle and examples of permissible conservative amino acid substitutions are further explained herein.

The fatty acid, being a half-life extending moiety, is attached in such a way so as enhance, and/or not to interfere with, the biological function of the constituent portions of the conjugates of the invention. E.g. The fatty acid moiety is attached to the amino functionality of the N-terminus of the peptide (when linker is absent) via one of its carboxylic acid functionality, forming an amide bond. Alternatively, the fatty acid moiety is attached to the amino functionality of the PEG linker (when linker is present) via one of its carboxylic acid functionality.

In one embodiment, the conjugates of the invention are particularly useful for the treatment or prevention of a disorder or condition associated with heart failure, or a disorder responsive to the activation (or agonism) of the APJ receptor activity. In another embodiment, the conjugates of the invention are useful in the treatment of acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In a preferred embodiment, the apelin conjugates of the invention is useful in the treatment of acute decompensated heart failure (ADHF). In another preferred embodiment, the apelin conjugates are useful in the treatment of chronic heart failure.

In another embodiment, the invention pertains to a method for treating disorder or disease responsive to the activation of the APJ receptor, in a subject in need of such treatment, comprising: administering to the subject an effective amount of a conjugate of the invention, such that the disorder or disease responsive to the activation of the APJ receptor in the subject is treated.

In yet another embodiment, the invention pertains to method of making the conjugates as described herein.

In yet another embodiment, the invention pertains to pharmaceutical compositions, comprising a conjugate of the invention and one or more pharmaceutically acceptable carriers.

In still another embodiment, the invention pertains to combinations including, a conjugate of the invention, and pharmaceutical combinations of one or more therapeutically active agents.

In another embodiment, the invention pertains to a method for activation of the APJ receptor in a subject in need thereof, comprising: administering to the subject a therapeutically effective amount of a conjugate of the invention.

These and other aspects of the invention will be elucidated in the following detailed description of the invention.

DETAILED DESCRIPTION OF THE INVENTION

Definition

For purposes of interpreting this specification, the following definitions will apply unless specified otherwise and whenever appropriate, terms used in the singular will also include the plural and vice versa.

As used herein, "disorders or diseases responsive to the modulation of the APJ receptor," "disorders and conditions responsive to the modulation of the APJ," "disorders and conditions responsive to the modulation of APJ receptor activity," "disorders responsive to the activation (or agonism) of the APJ receptor activity," and like terms include acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

The term "APJ" (also referred to as "apelin receptor," "angiotensin-like-1 receptor," "angiotensin II-like-1 receptor," and the like) indicates a 380 residue, 7 transmembrane domain, Gi coupled receptor whose gene is localized on the long arm of chromosome 11 in humans (NCBI Reference Sequence: NP_005152.1, and encoded by NCBI Reference Sequence: NM_005161). APJ was first cloned in 1993 from genomic human DNA using degenerate oligonucleotide primers (O'Dowd et al. Gene, 136:355-60, 1993) and shares significant homology with angiotensin II receptor type 1. Despite this homology however, angiotensin II does not bind APJ. Although orphan for many years, the endogenous ligand has been isolated and named apelin (Tatemoto et al., Biochem Biophys Res Commun 251, 471-6 (1998)).

As used herein, "Activation of APJ receptor activity," or "Activation of the APJ receptor," refers to an increase in the APJ receptor activity. The activation of the APJ receptor activity is also referred to as "agonism" of the APJ receptor, e.g., by administration of the conjugates of the invention.

The terms "apelin," indicates a 77 residue preprotein (NCBI Reference Sequence: NP_0059109.3, and encoded by NCBI Reference Sequence: NM_017413.3), which gets processed into biologically active forms of apelin peptides, such as apelin-36, apelin-17, apelin-16, apelin-13, apelin-12. The full length mature peptide, referred to as "apelin-36," comprises 36 amino acids, but the most potent isoform is the pyroglutamated form of a 13mer of apelin (apelin-13), referred to as "Pyr-1-apelin-13 or Pyr$^1$-apelin-13" Different apelin forms are described, for instance, in U.S. Pat. No. 6,492,324B1.

The term "APJ agonist peptide" or "apelin peptide" are used interchangeably and include "apelin" as defined above which has been modified to minimize degradation and to enhance serum stability as well as to provide a better developability profile. In certain embodiments, the "APJ agonist peptide" or "Apelin peptide" include peptide of Formula (I).

As used herein, the terms "peptide" or "polypeptide" are used interchangeably to refer to two or more amino acids linked together. The art-recognized three letter or one letter abbreviations are used to represent amino acid residues that constitute the peptides and polypeptides of the invention. Except when preceded with "D", the amino acid is an L-amino acid. When the one letter abbreviation is a capital letter, it refers to the L-amino acid. When the one letter abbreviation is a lower case letter, it refers to the D-amino acid. Groups or strings or amino acid abbreviations are used to represent peptides. Peptides are indicated with the N-terminus on the left and the sequence is written from the N-terminus to the C-terminus.

Peptides of the invention contain non-natural amino acids (i.e., compounds that do not occur in nature) and other amino acid analogs as are known in the art may alternatively be employed.

Certain non-natural amino acids can be introduced by the technology described in Deiters et al., J Am Chem Soc 125:11782-11783, 2003; Wang and Schultz, Science 301: 964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the non-natural amino acid of choice.

One of ordinary skill in the art will appreciate that various amino acid substitutions, e.g., conservative amino acid substitutions, may be made in the sequence of any of the polypeptides described herein, without necessarily decreasing its activity. As used herein, "amino acid commonly used as a substitute thereof" includes conservative substitutions (i.e., substitutions with amino acids of comparable chemical characteristics). For the purposes of conservative substitution, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Examples of amino acid substitutions include substituting an L-amino acid for its corresponding D-amino acid, substituting cysteine for homocysteine or other non natural amino acids having a thiol-containing side chain, substituting a lysine for homolysine, diaminobutyric acid, diaminopropionic acid, ornithine or other non natural amino acids having an amino containing side chain, or substituting an alanine for norvaline or the like.

The term "amino acid," as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

The term "naturally occurring" refers to materials which are found in nature and are not manipulated by man. Similarly, "non-naturally occurring," "un-natural," and the like, as used herein, refers to a material that is not found in nature or that has been structurally modified or synthesized by man. When used in connection with amino acids, the term "naturally occurring" refers to the 20 conventional amino acids (i.e., alanine (A or Ala), cysteine (C or Cys), aspartic acid (D or Asp), glutamic acid (E or Glu), phenylalanine (F or Phe), glycine (G or Gly), histidine (H or His), isoleucine (I or Ile), lysine (K or Lys), leucine (L or Leu), methionine (M or Met), asparagine (N or Asn), proline (P or Pro), glutamine (Q or Gln), arginine (R or Arg), serine (S or Ser), threonine (T or Thr), valine (V or Val), tryptophan (W or Trp), and tyrosine (Y or Tyr)).

The terms "non-natural amino acid" and "unnatural amino acid," as used herein, are interchangeably intended to represent amino acid structures that cannot be generated biosynthetically in any organism using unmodified or modified genes from any organism, whether the same or different. The terms refer to an amino acid residue that is not present in the naturally occurring (wild-type) apelin protein sequence or the sequences of the present invention. These include, but are not limited to, modified amino acids and/or amino acid analogues that are not one of the 20 naturally occurring amino acids, selenocysteine, pyrrolysine (Pyl), or pyrrolinecarboxy-lysine (Pcl, e.g., as described in PCT patent publication WO2010/48582). Such non-natural amino acid residues can be introduced by substitution of naturally occurring amino acids, and/or by insertion of non-natural amino acids into the naturally occurring (wild-type) Apelin protein sequence or the sequences of the invention. The non-natural amino acid residue also can be incorporated such that a desired functionality is imparted to the apelin molecule, for example, the ability to link a functional moiety (e.g., PEG). When used in connection with amino acids, the symbol "U" shall mean "non-natural amino acid" and "unnatural amino acid," as used herein.

In addition, it is understood that such "unnatural amino acids" require a modified tRNA and a modified tRNA synthetase (RS) for incorporation into a protein. These "selected" orthogonal tRNA/RS pairs are generated by a selection process as developed by Schultz et al. or by random or targeted mutation. As way of example, pyrroline-carboxy-lysine is a "natural amino acid" as it is generated biosynthetically by genes transferred from one organism into the host cells and as it is incorporated into proteins by using natural tRNA and tRNA synthetase genes, while p-aminophenylalanine (See, Generation of a bacterium with a 21 amino acid genetic code, Mehl R A, Anderson J C, Santoro S W, Wang L, Martin A B, King D S, Horn D M, Schultz P G. J Am Chem Soc. 2003 Jan. 29; 125(4):935-9) is an "unnatural amino acid" because, although generated biosynthetically, it is incorporated into proteins by a "selected" orthogonal tRNA/tRNA synthetase pair.

Modified encoded amino acids include, but are not limited to, hydroxyproline, γ-carboxyglutamate, O-phosphoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminoproprionic acid, N-ethylglycine, N-methylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. The term "amino acid" also includes naturally occurring amino acids that are metabolites in certain organisms but are not encoded by the genetic code for incorporation into proteins. Such amino acids include, but are not limited to, ornithine, D-ornithine, and D-arginine.

The term "amino acid analogue," as used herein, refers to compounds that have the same basic chemical structure as a naturally occurring amino acid, by way of example only, an α-carbon that is bound to a hydrogen, a carboxyl group, an amino group, and an R group. Amino acid analogues include the natural and unnatural amino acids which are chemically blocked, reversibly or irreversibly, or their C-terminal carboxy group, their N-terminal amino group and/or their side-chain functional groups are chemically modified. Such analogues include, but are not limited to, methionine sulfoxide, methionine sulfone, S-(carboxymethyl)-cysteine, S-(carboxymethyl)-cysteine sulfoxide, S-(carboxymethyl)-cysteine sulfone, aspartic acid-(beta-methyl ester), N-ethylglycine, alanine carboxamide, homoserine, norleucine, and methionine methyl sulfonium.

As used herein the term "amide" refers to an amide derivative of the carboxylic acid group at the C-terminus (e.g. —C(O)NH$_2$, —C(O)NH—C$_{1-6}$ alkyl, —C(O)NH—C$_{1-2}$alkylphenyl, —C(O)NH—NHBn or —C(O)N(C$_{1-6}$ alkyl)$_2$).

The term "amide" also refers to derivative of the amino group at the N-terminus (e.g. —carboxylic acid functionality of the fatty acid forming an amide bond with the amino functionality at the N-terminus of the apelin peptide).

As used herein, the term "ester" refers to an ester derivative of the carboxylic acid group at the C-terminus (e.g. —COOR) wherein R of the ester refers to C$_{1-6}$ alkyl groups such as methyl, ethyl, n-propyl, isopropyl, n-butyl, etc., C$_{3-8}$ cycloalkyl groups such as cyclopentyl, cyclohexyl, etc., C$_{6-10}$ aryl groups such as phenyl, α-naphthyl, etc., C$_{6-10}$ aryl-C$_{1-6}$ alkyl groups, for example phenyl-C$_{1-2}$ alkyl groups such as benzyl, phenethyl, benzhydryl, etc., and α-naphthyl-C$_{1-2}$ alkyl groups such as α-naphthylmethyl and the like. Mention may also be made of pivaloyloxymethyl ester and the like, which are commonly used as esters for oral administration. When the APJ agonist peptides of Formula I possess additional carboxyl or carboxylate groups in positions other than the C terminus, those polypeptides in which such groups are amidated or esterified also fall under the category of the polypeptide of the invention. In such cases, the esters may for example be the same kinds of esters as the C-terminal esters mentioned above.

The term "conjugate" and "bioconjugate" is used interchangeably and is intended to refer to the entity formed as a result of a covalent attachment of an APJ agonist polypeptide or a polypeptide of Formula I, and a fatty acid moiety, via an optional polyethylene glycol (PEG) linker.

The term "increased half-life" or "increase serum half-life" or "extending half-life" is meant the positive change in circulating half-life of a modified biologically active molecule (e.g. apelin 13 or analog) relative to its non-modified form (or naked form of the peptide). Serum half-life is measured by taking blood samples at various time points after administration of the biologically active molecule, and determining the concentration of that molecule in each sample. Measuring the change in serum concentration with time allows calculation of the serum half-life of a modified molecule (e.g. conjugated molecule). By comparing the serum half-life of a modified molecule (e.g. conjugated molecule), with an unmodified molecule (e.g. apelin 13 or analog thereof), the relative increase in serum half-life or t½ may be determined. The increase is desirably at least about two-fold, but a smaller increase may be useful.

Conjugates of the Invention

Various embodiments of the invention are described herein. It will be recognized that features specified in each embodiment may be combined with other specified features to provide further embodiments.

In embodiment 1, the invention therefore provides a conjugate, or a pharmaceutically acceptable salt thereof, comprising a. an APJ agonist peptide having the following formula (I):

Q-R-P-R-L-C*-H-K-G-P-(Nle)-C*-F  (I);

or an amide or ester thereof, or a peptide substantially equivalent thereto; wherein the two cysteine amino acids labeled with "*" form a disulfide bond between the thiol functionalities of their side chain; and 9
b. a fatty acid selected from:

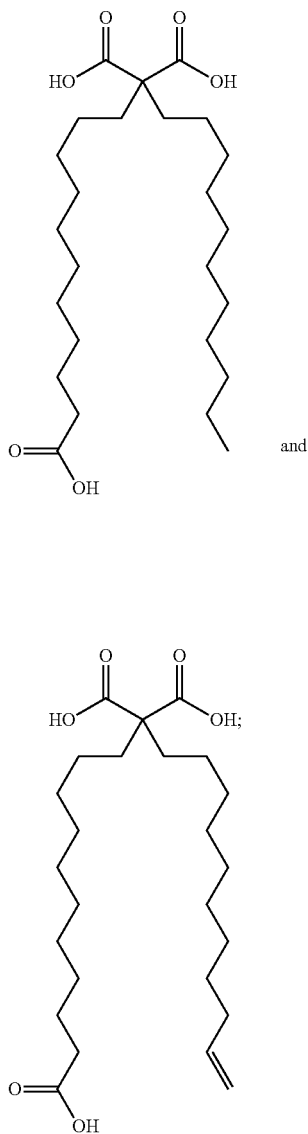

and wherein said fatty acid is covalently linked to the N-terminus of the peptide via one of its carboxylic acid functionality, optionally via a polyethylene glycol linker.

In embodiment 1A, the invention relates to a conjugate, or a pharmaceutically acceptable salt thereof, comprising:

a. an APJ agonist peptide having the following formula (I):

Q-R-P-R-L-C*-H-K-G-P-(Nle)-C*-F     (I);

wherein the two cysteine amino acids labeled with "*" form a disulfide bond between the thiol functionalities of their side chain; and 10
b. a fatty acid selected from:

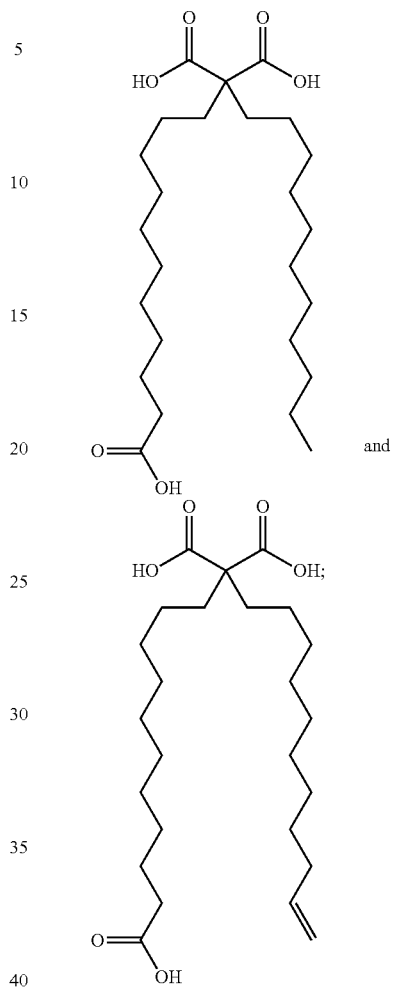

and wherein said fatty acid is covalently linked to the N-terminus of the peptide via one of its carboxylic acid functionality, optionally via a polyethylene glycol linker.

Fatty acids described in embodiment 1 or 1A have been described in U.S. provisional application No. 62/082,327.

Any polyethylene glycol linker group is optional. The linker is polymeric in nature and is a polyethylene glycol moiety that contains two reactive groups/functional groups, one of which can react with the polypeptide of Formula I and the other with the fatty acid moiety.

In embodiment 2, the invention related to a conjugate according to embodiment 1 or 1A, wherein the Polyethylene glycol (PEG) linker is present and is of Formula (III):

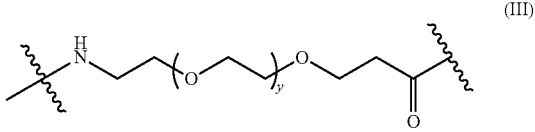

(III)

wherein y is 1-30, wherein the carbonyl functionality of the PEG linker forms an amide bond with the amino functionality at the N-terminus of the peptide of Formula (I) and wherein the amino functionality of the PEG linker forms an amide bond with one of the carboxylic acid functionalities of the fatty acid.

In embodiment 3, the invention related to a conjugate according to embodiment 1, 1A or 2 wherein the polyethylene glycol linker is of Formula (III) and y is 2 to 25.

In embodiment 4, the invention relates to a conjugate according to any one of the previous embodiments wherein the fatty acid is:

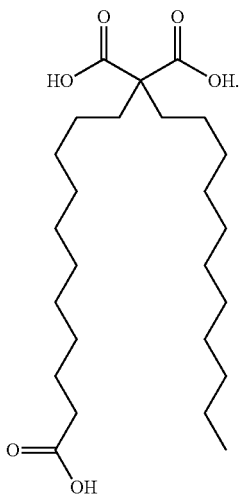 [SMILES: CCCCCCCCCCCC(CCCCCCCCCCC(=O)O)(C(=O)O)C(=O)O]

In embodiment 5, the invention relates to a conjugate according to any one of the previous embodiments wherein the fatty acid is attached to the amino functionality of the PEG linker, or to the amino functionality at the N-terminus of the peptide if the PEG linker is absent, via one of its geminal carboxylic acid functionality. This is represented by the following Formulae showing the point of attachment to the linker or to the N-terminus of the peptide:

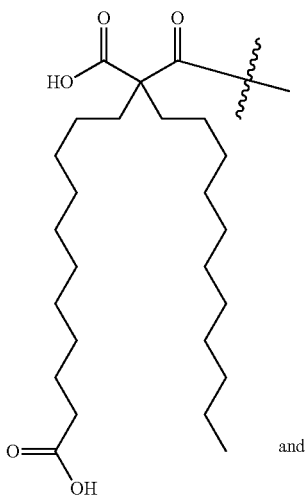

and

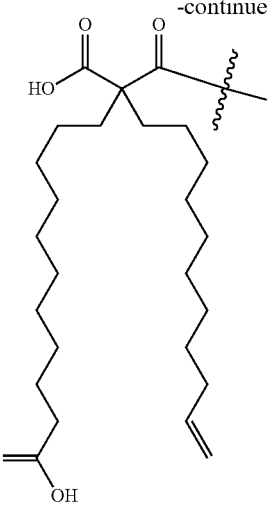

In embodiment 6, the invention relates to a conjugate according to any one of embodiments 1-4 wherein the fatty acid is attached to the amino functionality of the PEG linker, or to the amino functionality of the peptide if the PEG linker is absent, via its terminal carboxylic acid functionality. This is represented by the following Formulae showing the point of attachment to the linker or to the N-terminus of the peptide:

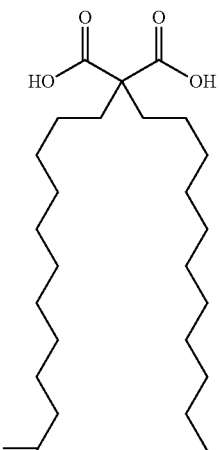

and

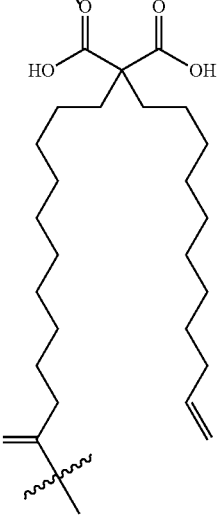

In embodiment 7, the invention pertains to a conjugate according to embodiment 1 or 1A selected from the following:

In embodiment 7A, the conjugates of the invention demonstrate: 1. substantially equivalent or improved activity as compared to wild type apelin, apelin-13, pyr-1-apelin-13

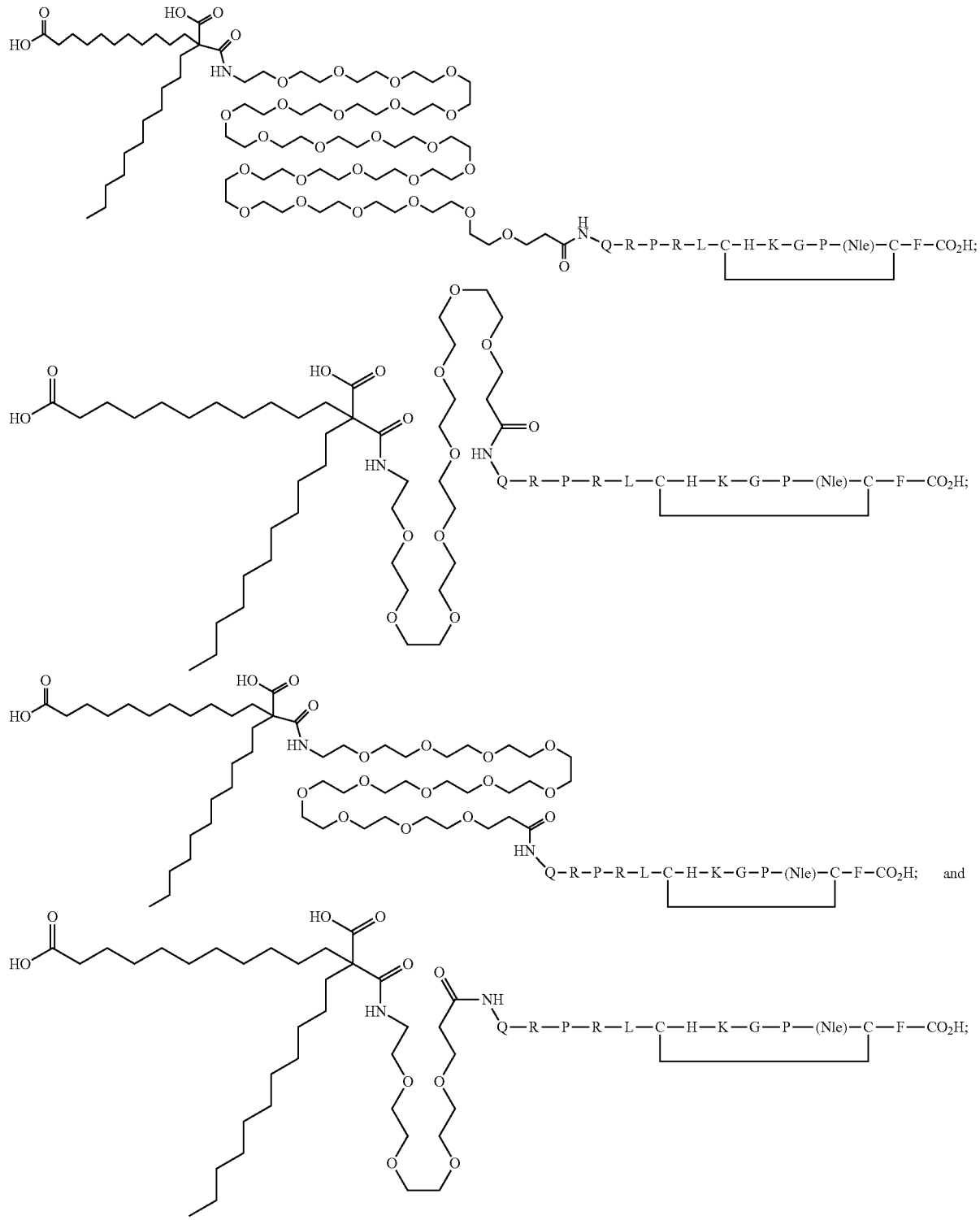

or a pharmaceutically acceptable salt thereof.

Unless specified otherwise, the term "polypeptide" or "peptide", "APJ peptide agonists," and the like refers to a polypeptide of Formula (I) or an amide, an ester or a pharmaceutically acceptable salt thereof.

and/or corresponding naked (non-conjugated) apelin peptide of Formula (I) or analog thereof; and/or 2. improved plasma stability over wild type apelin, apelin-13, pyr-1-apelin-13 and/or over the corresponding naked (non-conjugated) apelin peptide of Formula (I) or analog thereof.

In embodiment 7B, the conjugates of the invention demonstrates: 1. substantially equivalent or improved activity over apelin conjugates described in U.S. patent application Ser. No. 14/336,293 and/or over apelin fatty acid conjugates described in U.S. application Ser. No. 14/336,262; and/or 2. Equivalent or improved plasma stability over apelin conjugates, more specifically over apelin conjugates described in U.S. patent application Ser. No. 14/336,293 and/or over apelin fatty acid conjugates described in U.S. application Ser. No. 14/336,262.

In one aspect of embodiments 7A and 7B, the plasma stability improvement is at least 2 fold.

In embodiment 7C, the fatty acid conjugate of the invention has a plasma stability of at least 30 minutes. In another embodiment, the fatty acid conjugate of the invention has a plasma stability of at least 60 minutes. In another embodiment, the fatty acid conjugate of the invention has a plasma stability of at least 5 h, preferably at least 10 h and more preferably at least 12 h.

In embodiment 7D, the apelin fatty acid conjugates of the invention has an $EC_{50}$ of less than 400 nM. In another embodiment the apelin fatty acid conjugates of the invention has an $EC_{50}$ of less than 300 nM, preferably less than 200 nM and more preferably less than 160 nM. In yet another embodiment, the apelin fatty acid conjugates of the present invention has an $EC_{50}$ of less than 100 nM.

The apelin fatty acid conjugates of the invention also encompass apelin fatty acid conjugates that are substantially equivalent thereto. The apelin fatty acid conjugates of the invention also encompass conjugates containing apelin peptides which are at least about 95% identical to peptides according to Formulae I, or an amide, an ester or a salt thereof.

As used herein, the phrase "homologous amino acid sequence," or variations thereof, refers to sequences characterized by a homology, at the amino acid level, of at least a specified percentage and is used interchangeably with "sequence identity." Homologous amino acid sequences include those amino acid sequences which contain conservative amino acid substitutions and which polypeptides have the same binding and/or activity. In some embodiments, an amino acid sequence is homologous if it has at least 60% or greater, up to 99%, identity with a comparator sequence. In some embodiments, an amino acid sequence is homologous if it shares one or more, up to 60, amino acid substitutions, additions, or deletions with a comparator sequence. In some embodiments, the homologous amino acid sequences have no more than 5 or no more than 3 conservative amino acid substitutions.

Homology may also be at the polypeptide level. The degree or percentage identity of peptides or polypeptides of the invention, or portions thereof, and different amino acid sequences is calculated as the number of exact matches in an alignment of the two sequences divided by the length of the "invention sequence" or the "foreign sequence", whichever is shortest. The result is expressed as percent identity.

A conjugate comprising a polypeptide having an amino acid sequence with a homology of about 80-99.9%, preferably 90-99.9% to the amino acid sequence of Formula I, and possessing a plasma stability superior to apelin-13 and/or pyr-1-apelin-13 and/or corresponding unconjugated peptide, fall under the category of the conjugate of the invention.

A conjugate variant possessing a somewhat decreased level of activity relative to apelin-13 and/or pyr-1-apelin-13 and/or corresponding unconjugated peptide can nonetheless be considered to be functional and biological variants, although ideally, a biologically active conjugate possesses similar or enhanced biological properties relative to apelin-13 and/or pyr-1-apelin-13 and/or corresponding unconjugated peptide.

The term "substantially equivalent" means the nature of the receptor-binding activity, signal transduction activity and the like is equivalent. Thus, it is allowable that even differences among grades such as the strength of receptor binding activity and the molecular weight of the polypeptide are present.

A polypeptide as described herein, or a substantial equivalent thereto, by substitution, deletion, addition or insertion of one or more of amino acids may be mentioned as polypeptides containing an amino acid sequence substantial equivalent(s) in the above sense. A polypeptide as described herein, or a substantial equivalent thereto, by substitution of 1 to 5, preferably 1 to 3 and more preferably 1 or 2 amino acids with natural or un-natural amino acids may be mentioned as polypeptides containing an amino acid sequence substantial equivalent(s) in the above sense. Preferably the 2 cysteines forming the disulfur bridge are not been substituted. Further modifications and alterations may include the replacement of an L-amino-acid with a D-amino acid, or other variation including, but not limited to, phosphorylation, carboxylation, alkylation and the like as long as the APJ agonistic activity of the conjugate comprising such peptide is maintained and the plasma stability is improved over the pyroglutamated form of apelin-13 and/or improved over the corresponding non-conjugated peptide.

Preparation of the Peptide of Formula I:

The apelin peptide of Formula I may be produced by either synthetic chemical processes or by recombinant methods or combination of both methods. The Apelin peptides and/or peptide-linker constructs may be prepared as full-length or may be synthesized as non-full length fragments and joined. The peptide of the present invention can be produced by the per se known procedures for peptide synthesis. The methods for peptide synthesis may be any of a solid-phase synthesis and a liquid-phase synthesis. Thus, the peptide and polypeptide of interest can be produced by condensing a partial peptide or amino acid capable of constituting the protein with the residual part thereof and, when the product has a protective group, the protective group is detached whereupon a desired peptide can be manufactured. The known methods for condensation and deprotection include the procedures described in the following literature (1)-(5).

(1) M. Bodanszky and M. A. Ondetti, Peptide Synthesis, Interscience Publishers, New York, 1966,
(2) Schroeder and Luebke, The Peptide, Academic Press, New York, 1965,
(3) Nobuo Izumiya et al. Fundamentals and Experiments in Peptide Synthesis, Maruzen, 1975,
(4) Haruaki Yajima and Shumpei Sakakibara, Biochemical Experiment Series 1, Protein Chemistry IV, 205, 1977, and
(5) Haruaki Yajima (ed.), Development of Drugs-Continued, 14, Peptide Synthesis, Hirokawa Shoten.

After the reaction, the peptide can be purified and isolated by a combination of conventional purification techniques such as solvent extraction, column chromatography, liquid chromatography, and recrystallization. Where the peptide isolated as above is a free compound, it can be converted to a suitable salt by the known method. Conversely where the isolated product is a salt, it can be converted to the free peptide by the known method.

The amide of polypeptide can be obtained by using a resin for peptide synthesis which is suited for amidation. The resin includes chloromethyl resin, hydroxymethyl resin, benzhydrylamine resin, aminomethyl resin, 4-benzyloxybenzyl alcohol resin, 4-methylbenz-hydrylamine resin, PAM resin, 4-hydroxymethylmethylphenylacetamidomethyl resin, polyacrylamide resin, 4-(2',4'-dimethoxyphenyl-hydroxymethyl)phenoxy resin, 4-(2',4'-dimethoxyphenyl-Fmoc-aminomethyl)phenoxy resin, 2-chlorotrityl chloride resin, and so on. Using such a resin, amino acids whose α-amino groups and functional groups of side-chain have been suitably protected are condensed on the resin according to the sequence of the objective peptide by various condensation techniques which are known per se. At the end of the series of reactions, the peptide or the protected peptide is removed from the resin and the protective groups are removed and if necessary, disulfide bonds are formed to obtain the objective polypeptide.

For the condensation of the above-mentioned protected amino acids, a variety of activating reagents for peptide synthesis can be used such as HATU, HCTU or e.g. a carbodiimide. The carbodiimide includes DCC, N,N'-diisopropylcarbodiimide, and N-ethyl-N'-(3-dimethylaminopropyl)carbodiimide. For activation with such a reagent, a racemization inhibitor additive, e.g. HOBt or Oxyma Pure can be used. The protected amino acid can be directly added to the resin along with the activation reagents and racemization inhibitor or be pre-activated as symmetric acid anhydride, HOBt ester, or HOOBt ester then added to the resin. The solvent for the activation of protected amino acids or condensation with the resin can be properly selected from among those solvents which are known to be useful for peptide condensation reactions. For example, N,N-dimethylformamide, N-methylpyrrolidone, chloroform, trifluoroethanol, dimethyl sulfoxide, DMF, pyridine, dioxane, methylene chloride, tetrahydrofuran, acetonitrile, ethyl acetate, or suitable mixtures of them can be mentioned.

The reaction temperature can be selected from the range hitherto-known to be useful for peptide bond formation and is usually selected from the range of about −20° C.-50° C. The activated amino acid derivative is generally used in a proportion of 1.5-4 fold excess. If the condensation is found to be insufficient by a test utilizing the ninhydrin reaction, the condensation reaction can be repeated to achieve a sufficient condensation without removing the protective group. If repeated condensation still fails to provide a sufficient degree of condensation, the unreacted amino group can be acetylated with acetic anhydride or acetylimidazole.

The protecting group of amino group for the starting material amino acid includes Z, Boc, tertiary-amyloxycarbonyl, isobornyloxycarbonyl, 4-methoxybenzyloxycarbonyl, Cl—Z, Br—Z, adamantyloxycarbonyl, trifluoroacetyl, phthalyl, formyl, 2-nitrophenylsulfenyl, diphenylphosphinothioyl, or Fmoc. The carboxy-protecting group that can be used includes but is not limited to the above-mentioned $C_{1-6}$ alkyl, $C_{3-8}$ cycloalkyl and $C_{6-10}$aryl-$C_{1-2}$alkyl as well as 2-adamantyl, 4-nitrobenzyl, 4-methoxybenzyl, 4-chlorobenzyl, phenacyl, benzyloxycarbonylhydrazido, tertiary-butoxycarbonylhydrazido, and tritylhydrazido.

The hydroxy group of serine and threonine can be protected by esterification or etherification. The group suited for said esterification includes carbon-derived groups such as lower alkanoyl groups, e.g. acetyl etc., aroyl groups, e.g. benzoyl etc., benzyloxycarbonyl, and ethoxycarbonyl. The group suited for said etherification includes benzyl, tetrahydropyranyl, and tertiary-butyl. The protective group for the phenolic hydroxyl group of tyrosine includes Bzl, $Cl_2$-Bzl, 2-nitrobenzyl, Br—Z, and tertiary-butyl.

The protecting group of imidazole for histidine includes Tos, 4-methoxy-2,3,6-tri ethylbenzenesulfonyl, DNP, benzyloxymethyl, Bum, Boc, Trt, and Fmoc.

The activated carboxyl group of the starting amino acid includes the corresponding acid anhydride, azide and active esters, e.g. esters with alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide, HOBt, etc. The activated amino group of the starting amino acid includes the corresponding phosphoramide.

The method for elimination of protective groups includes catalytic reduction using hydrogen gas in the presence of a catalyst such as palladium black or palladium-on-carbon, acid treatment with anhydrous hydrogen fluoride, methanesulfonic acid, trifluoromethanesulfonic acid, trifluoroacetic acid, or a mixture of such acids, base treatment with diisopropylethylamine, triethylamine, piperidine, piperazine, reduction with sodium metal in liquid ammonia. The elimination reaction by the above-mentioned acid treatment is generally carried out at a temperature of −20° C.-40° C. and can be conducted advantageously with addition of a cation acceptor such as anisole, phenol, thioanisole, m-cresol, p-cresol, dimethyl sulfide, 1,4-butanedithiol, 1,2-ethanedithiol. The 2,4-dinitrophenyl group used for protecting the imidazole group of histidine can be eliminated by treatment with thiophenol, while the formyl group used for protecting the indole group of tryptophan can be eliminated by alkali treatment with dilute sodium hydroxide solution or dilute aqueous ammonia as well as the above-mentioned acid treatment in the presence of 1,2-ethanedithiol, 1,4-butanedithiol.

The method for protecting functional groups which should not take part in the reaction of the starting material, the protective groups that can be used, the method of removing the protective groups, and the method of activating the functional groups that are to take part in the reaction can all be selected judicially from among the known groups and methods.

An another method for obtaining the amide form of the polypeptide comprises amidating the -carboxyl group of the C-terminal amino acid at first, then extending the peptide chain to the N-side until the desired chain length, and then selectively deprotecting the α-amino group of the C-terminal peptide and the α-carboxy group of the amino acid or peptide that is to form the remainder of the objective polypeptide and condensing the two fragments whose α-amino group and side-chain functional groups have been protected with suitable protective groups mentioned above in a mixed solvent such as that mentioned hereinbefore. The parameters of this condensation reaction can be the same as described hereinbefore. From the protected peptide obtained by condensation, all the protective groups are removed by the above-described method to thereby provide the desired crude peptide. This crude peptide can be purified by known purification procedures and the main fraction be lyophilized to provide the objective amidated polypeptide. To obtain an ester of the polypeptide, the a-carboxyl group of the C-terminal amino acid is condensed with a desired alcohol to give an amino acid ester and then, the procedure described above for production of the amide is followed.

Synthesis of the Fatty Acid Moieties

Schemes 1 describes the synthesis of a fatty acid moiety according to embodiment 1.

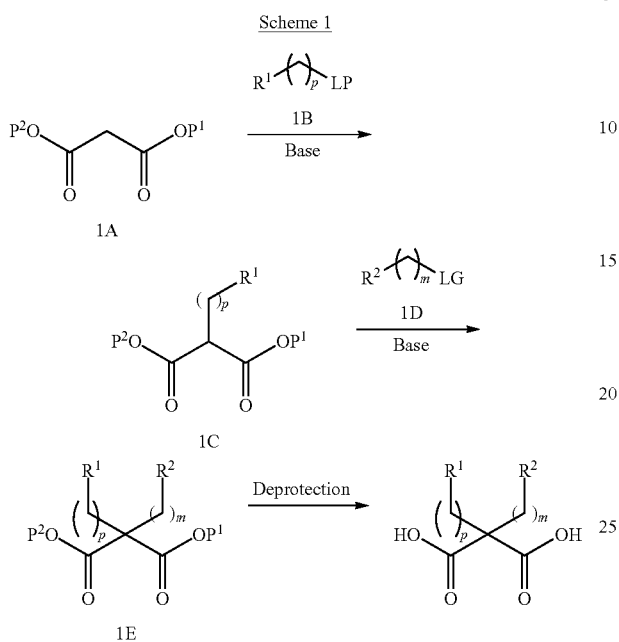

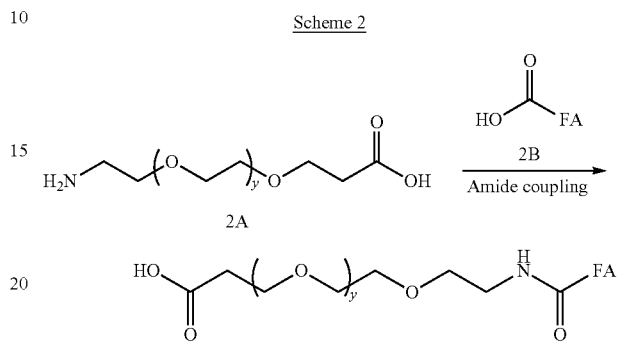

wherein $P^1$ and $P^2$ are carboxylic acid protective group such as for example methyl, ethyl, tert-butyl, methoxybenzyl, benzyl, benzyloxy, methoxymethyl, methylthiomethyl, tetrahydropyranyl, phenacyl, N-Phthalimide, cinnamyl, triphenylmethyl, 9-anthrylmethyl, piperonyl, trimethylsilyl, t-butyldimethylsilyl or 2-alkyl 1,3 oxazolines; wherein LG is a leaving group such as for example halo (e.g. Br, Cl, I) or trifluoromethanesulfonyloxy and wherein $R^1$ is $CH_3$ and p is 10 or $R^1$ is $CH=CH_2$ and p is 9 and wherein m is 10 and $R^2$ is $CO_2H$; as described in embodiment 1.

Alkylation of protected malonic acid (1A) with an alkylating agent (1B) in the presence of a base (e.g. sodium hydride, potassium or cesium carbonates, sodium hydroxide, lithium diisopropyl amide, sodium bis(trimethylsilyl)amide, potassium bis(trimethylsilyl)amide, lithium tertamethylpiperidide, 1,8-Diaazacycloundec-7-ene, N,N-diisopropyl ethyl amine or 2,6-dit-butylputridine), in a solvent such as DMF, THF or dimethyl acetamide, generates the protected di-acid moiety (1C).

Protected di-acid moiety (1C) undergoes a second alkylation with alkylating agent (1D) under basic condition as described above, in order to obtain dialkylated protected product (1E). The fatty acids according to embodiment 1 are obtained by deprotection using appropriate deprotection method. Standard methods can be applied for the hydrolysis of the intermediate (1E) using a base selected from, but not limited to, NaOH, KOH, or LiOH, or an acid selected from, but not limited to, TFA, HCl, or $BCl_3$. When $P^1$ or $P^2$ is benzyl or methoxybenzyl, a preferable method of the deprotection is hydrogenation in the presence of a catalyst such as, but not limited to, palladium-on-carbon.

The order of the two alkylation steps may be reversed. Additionally, with $R_2$ being $CO_2H$, protection of this functional group may be required prior to the alkylation step. Protective groups for acid carboxylic are known in the art (for example benzyl group).

More specific examples of fatty acids syntheses have been described in the experimental section infra and in provisional application No. 62/082,327.

Synthesis of Fatty Acid (FA)-PEG Linker Construct:

Scheme 2 describes the synthesis of a fatty acid-PEG linker construct with a terminal CO2H functional group.

wherein FA is a fatty acid of Formulae:

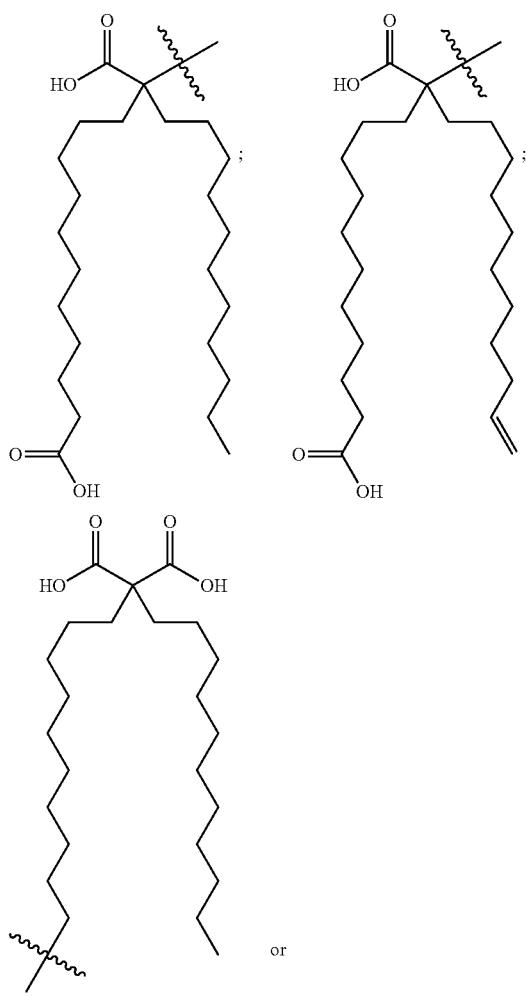

-continued

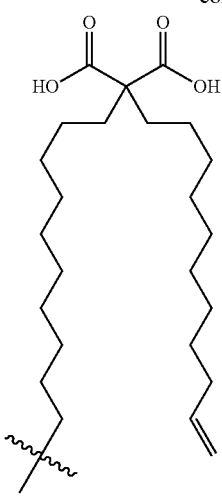

or a protected form thereof, and y is 1 to 30. Protecting groups for carboxylic acid have been described supra in Scheme 1.

The fatty acid (2B) may be attached to a PEG containing linker (2A) using peptide condensation reagents including, but not limited to, dicyclohexylcarbodiimide (DCC), diisopropylcarbodiimide (DIC), 1-ethyl-3-(3-dimethylamino-propyl)carbodiimide hydrochloride (EDC HCl), benzotriazole-1-yl-oxy-tris-pyrrolidino-phosphonium hexafluorophosphate (PyBOP), or benzotriazole-1-yl-oxy-tris-(dimethylamino)-phosphonium hexafluorophosphate (BOP) in presence of or absence of a reagent such as 1-hydroxybenzotriazole, 1-hydroxy-7-azabenzotriazole, or dimethylaminopyridine. Preferably, the acid functionality of (2B) is converted to its activated form thereof using NHS chemistry prior to reacting with the amino functionality of the PEG linker (2A).

In the presence of additional carboxylic functionalities on both the fatty acid and the PEG linker, protecting groups may be introduced prior to the coupling reaction in order to control the reactive site. Protecting group for carboxylic acid are described supra in scheme 1. Alternatively, selective activation of carboxylic acid can be achieved using NHS chemistry.

More specific examples of fatty acid-PEG constructs syntheses have been described in the experimental section infra and in provisional application No. 62/082,327.

Preparation of Conjugates

Scheme 3 describes the conjugation of the fatty acid or the fatty acid-PEG construct to the amino functionality at the N-terminus of the Apelin peptide of Formula I:

Conjugation Via Direct Attachment Using Coupling Conditions

Scheme 3

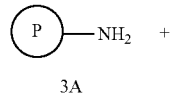

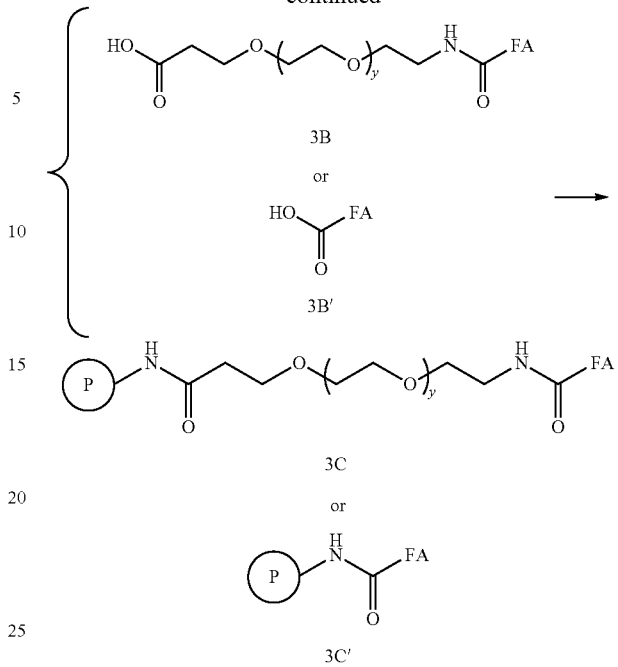

wherein P is the apelin peptide of Formula I and the fatty acid or the fatty acid-PEG construct is attached to the N-terminus of the biomolecule, and wherein FA is as defined supra in scheme 2.

The fatty acid-linker construct (3B) or the fatty acid (3B') is attached to an amino residue of the peptide (3A) (the amino functionality of the N-terminus) via its carboxylic acid reactive group using standard amide coupling methods. Known coupling methods have been described in detail supra in Scheme 2. Preferably the acid functionality on the fatty acid (3B') or on the fatty acid-PEG construct (3B) is activated using NHS chemistry.

More detailed experimental conditions have been described in the experimental section infra and in the U.S. provisional application No. 62/082,327.

Pharmaceutical Compositions

The conjugate of the instant invention may be administered in any of a variety of ways, including subcutaneously, intramuscularly, intravenously, intraperitoneally, inhalationally, intranasally, orally etc. Particularly preferred embodiments of the invention employ continuous intravenous administration of the conjugates of the instant invention, or an amide, ester, or salt thereof. Another preferred embodiments of the invention employ subcutaneous administration of the conjugates of the invention, or an amide, ester or salt thereof.

The conjugates of the instant invention may be administered as a bolus or as a continuous infusion over a period of time. An implantable pump may be used. In certain embodiments of the invention, intermittent or continuous conjugates administration is continued for one to several days (e.g., 2-3 or more days), or for longer periods of time, e.g., weeks, months, or years. In some embodiments, intermittent or continuous conjugates administration is provided for at least about 3 days. In other embodiments, intermittent or continuous conjugate administration is provided for at least about one week. In other embodiments, intermittent or continuous conjugate administration is provided for at least about two weeks. It may be desirable to maintain an average plasma conjugate concentration above a particular threshold value either during administration or between administration of multiple doses. A desirable concentration may be determined, for example, based on the subject's physiological condition, disease severity, etc. Such desirable value(s) can be identified by performing standard clinical trials. Alternatively, the peptides and conjugates thereof could be delivered orally via FcRn mechanism. (Nat Rev Immunol. 7(9), 715-25, 2007; Nat Commun. 3; 3:610, 2012, Am J Physiol Gastrointest Liver Physiol 304: G262-G270, 2013).

In another aspect, the present invention provides a pharmaceutical composition comprising a conjugate of the present invention or and amide, an ester or a salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, lyophilizates, powders or suppositories), or in a liquid form (including without limitation solutions, suspensions or emulsions). The pharmaceutical compositions can be subjected to conventional pharmaceutical operations such as aseptic manufacturing, sterilization and/or can contain conventional inert diluents, cake forming agents, tonicity agents, lubricating agents, or buffering agents, as well as adjuvants, such as preservatives, stabilizers, wetting agents, emulsifers and buffers, etc.

In certain embodiments, the pharmaceutical composition is for subcutaneous administration. Suitable formulation components and methods for subcutaneous administration of protein/polypeptides are known in the art. See e.g., Published US Patent application No 2011/0044977 and U.S. Pat. Nos. 8,465,739 and 8,476,239. Typically, the pharmaceutical compositions for subcutaneous administration contain suitable stabilizers (e.g. amino acids, such as methionine, and or saccharides such as sucrose), buffering agents and tonicifying agents.

Pharmaceutical compositions suitable for injectable use typically include sterile aqueous solutions (where water soluble) or dispersions and sterile powders for the extemporaneous preparation of sterile injectable solutions or dispersion.

For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, amino acids, sorbitol, sodium chloride in the composition. Prolonged absorption of the injectable compositions can be brought about by including in the composition an agent which delays absorption, for example, aluminum monostearate and gelatin.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Sterile injectable solutions can be prepared by incorporating the active compound in the required amount in an appropriate solvent with one or a combination of ingredients enumerated above, as required, followed by filtration sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable salts" refers to salts that retain the biological effectiveness and properties of the conjugates of this invention and, which typically are not biologically or otherwise undesirable. In many cases, the conjugates of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Method of the Invention:

Apelin family of peptides is the only known natural family of ligands for the G protein coupled APJ receptor. Apelin gene encodes a 77 amino acid polypeptide, which gets processed into biologically active forms of apelin peptides, such as apelin-36, apelin-17, apelin-16, apelin-13, apelin-12 and pyroglutamate modified form of apelin-13 ($Pyr^1$-apelin-13). Any one of these apelin peptides, upon binding to APJ receptor, transduces the signal via Gi and Gq proteins. In cardiomyocytes, Gi or Gq coupling leads to changes in intracellular pH, PLC activation, and IP3 production that enhance myofilament calcium sensitivity and ultimately result in increased cardiac contractility. Gi coupling inhibits activated Gs, adenylyl cyclase and cAMP production and increases pAkt levels leading to cardioprotection. In vascular endothelial cells, APJ activation via Gi, pAKT leads to increased nitric oxide (NO) production, which increases smooth muscle relaxation resulting in overall vasodilation.

Patients with chronic stable heart failure have occasional acute episodes of decompensation, where cardiac contractility declines further and symptoms worsen. These exacerbations are referred to as acute decompensated heart failure (ADHF). Current therapies for ADHF include diuretics, vasodilators, and inotropes, which directly increase cardiac contractility. Current intravenous inotropes (dobutamine, dopamine, milrinone, levosimendan) are well known for their adverse events such as arrhythmia and increased long-term mortality. The synthetic apelin fatty acid conjugate analogs of the instant invention provide a therapy for ADHF that increases cardiac contractility without arrhythmogenic or mortality liabilities and address the enormous unmet medical need in chronic heart failure.

Indeed, acute apelin treatment (5 min) in humans results in coronary vasodilatation and improved cardiac output. However, native apelins exhibit a very short $t_{1/2}$ (seconds) and duration of action (few minutes) in vivo. The potent synthetic conjugate APJ agonists of the instant invention have longer half lives compared to the native apelin and/or compared to previously described synthetic apelin peptides and/or synthetic apelin fatty acid conjugates such as those described in U.S. Pat. No. 8,673,848 and U.S. patent application Ser. No. 14/336,293 respectively.

Activation of APJ receptor in cardiomyocytes a) improve cardiac contractility via Gi/Gq, PLC and Ca2+, and b) provide cardioprotection via Gi, pAkt activation, but without increasing cAMP (as seen with other inotropes). In addition, APJ agonism in endothelial cells leads to arterial vasodilation, which further benefits heart failure by unloading the work of left ventricle. Taken together the conjugates of the instant invention can improve overall cardiac function, reduce arrhythmogenesis and provide survival benefit.

More recently, there have been a number of preclinical research publications focusing on the potential involvement of Apelin in diabetes and insulin resistance. Apelin has been shown to 1) lower blood glucose levels by improving glucose uptake in muscle, adipose and heart, 2) protect pancreatic beta cells from ER stress and subsequent apoptosis, 3) lower the insulin secretion in beta cells, and 4) regulate catecholamine induced lypolysis in adipose tissue. Activation of pAKT pathway has been implicated in these processes.

The conjugates comprising polypeptide of Formula I, in free form or in pharmaceutically acceptable salt form, exhibit valuable pharmacological properties, e.g. APJ receptor agonism properties, e.g. as indicated in in vitro and in vivo tests as provided in the next sections and are therefore indicated for therapy.

Conjugates of the invention or a pharmaceutically acceptable salt thereof, may be useful in the treatment of an indication selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Thus, as a further embodiment, the present invention provides the use of a conjugate as described herein, or a pharmaceutically acceptable salt thereof for the treatment of a disease which is associated with the APJ receptor activity. In a further embodiment, the therapy is selected from a disease which is responsive to the agonism of the APJ receptor. In another embodiment, the disease is selected from the afore-mentioned list, suitably acute decompensated heart failure. In yet another subset of this embodiment, the present invention provides the use of conjugates as described herein, or a pharmaceutically acceptable salt thereof, in the manufacture of a medicament, for the treatment of a disease which is associated with the APJ receptor activity.

Thus, as a further embodiment, the present invention provides the use of a conjugate or a pharmaceutically acceptable salt thereof, in therapy. In a further embodiment, the therapy is selected from a disease which may be treated by activation (agonism) of the APJ receptor.

In another embodiment, the invention provides a method of treating a disease which is responsive to the agonism of the APJ receptor, comprising administration of a therapeutically acceptable amount of a conjugate according to anyone of embodiments 1 to 7D or a pharmaceutically acceptable salt thereof. In a further embodiment, the disease is selected from the afore-mentioned list, suitably acute decompensated heart failure.

In yet another subset of this embodiment, the invention provides a method of treating a disease which is associated with the activity of the APJ receptor comprising administration of a therapeutically acceptable amount of a conjugate according to anyone of embodiments 1 to 7D, or a pharmaceutically acceptable salt thereof.

The effective amount of a pharmaceutical composition or combination of the invention to be employed therapeutically will depend, for example, upon the therapeutic context and objectives. One skilled in the art will appreciate that the appropriate dosage levels for treatment will thus vary depending, in part, upon the molecule delivered, the indication for which the conjugate is being used, the route of administration, and the size (body weight, body surface, or organ size) and condition (the age and general health) of the patient. Accordingly, the clinician can titer the dosage and modify the route of administration to obtain the optimal therapeutic effect. A typical dosage can range from about 0.1 µg/kg to up to about 100 mg/kg or more, depending on the factors mentioned above. In other embodiments, the dosage can range from 0.1 µg/kg up to about 100 mg/kg; or 1 µg/kg up to about 100 mg/kg.

The frequency of dosing will depend upon the pharmacokinetic parameters of the dual function protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The term "a therapeutically effective amount" of a conjugate of the present invention refers to an amount of the conjugate of the present invention that will elicit the biological or medical response of a subject, for example, amelioration of a symptom, alleviation of a condition, slow or delay disease progression, or prevention of a disease, etc. In one non-limiting embodiment, the term "a therapeutically effective amount" refers to the amount of the bioconjugate of the present invention that, when administered to a subject, is effective to (1) at least partially alleviate, inhibit, prevent and/or ameliorate a condition, a disorder or a disease or a symptom thereof (i) ameliorated by the activation of the APJ receptor or (ii) associated with the activity of the APJ receptor, or (iii) characterized by abnormal activity of the APJ receptor; or (2) activate the APJ receptor.

In another non-limiting embodiment, the term "a therapeutically effective amount" refers to the amount of the bioconjugate of the present invention that, when administered to a cell, or a tissue, or a non-cellular biological material, or a medium, is effective to at least partially activate the APJ receptor. As will be appreciated by those of ordinary skill in the art, the absolute amount of a particular agent that is effective may vary depending on such factors as the desired biological endpoint, the agent to be delivered, the target tissue, etc. Those of ordinary skill in the art understand that "a therapeutically effective amount" may be administered in a single dose or may be achieved by administration of multiple doses. For example, in the case of an agent to treat heart failure, an effective amount may be an amount sufficient to result in clinical improvement of the patient, e.g., increased exercise tolerance/capacity, increased blood pressure, decrease fluid retention, and/or improved results on a quantitative test of cardiac functioning, e.g., ejection fraction, exercise capacity (time to exhaustion), etc.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the terms "prevent", "preventing" and "prevention" refer to the prevention of the recurrence, onset, or development of one or more symptoms of a disorder in a subject resulting from the administration of a therapy (e.g., a therapeutic agent), or the administration of a combination of therapies (e.g., a combination of therapeutic agents).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

The activity of a conjugate according to the present invention can be assessed by the following in vitro methods described below.

hAPJ Calcium Flux Assay:

Chem-5 APJ stable cells (Millipore # HTS068C) were plated in 384-well format with 10,000 cells/well in 25 ul growth media, then grown 24 hours in a 37° C. tissue culture incubator. One hour before the assay, 25 ul/well FLIPR Calcium 4 dye (Molecular Devices R8142) with 2.5 mM probenecid was added, and cells were incubated one hour in a 37° C. tissue culture incubator. Bioconjugates were solubilized in HBSS, HEPES & 0.1% BSA buffer, and serially-diluted 10-fold, from 50 uM to 5 pM, in triplicate. FLIPR Tetra was used to add bioconjugates to the cells with dye (1:5, for final bioconjugate concentrations ranging from 10 uM to 1 pM). FLIPR dye inside the cells emitted fluorescence after binding to calcium, while fluorescence from outside the cells was masked. Fluorescence was measured using 470-495 excitation and 515-575 emission wavelengths on the FLIPR Tetra. Readings were done for 3 minutes total, beginning 10 seconds before the bioconjugate addition. Maximum-minimum values were calculated and plotted for each bioconjugate concentration, and GraphPad prism software was used to calculate $EC_{50}$ values at the curve inflection points, for calcium flux stimulation by bioconjugates.

Plasma Stability Assay:

Materials:

Working solution: 1 mg/mL test article is prepared in Milli-Q water

Extraction solution: Methanol:Acetonitrile:Water (1:1:1) with 0.1% Formic Acid and 400 ng/mL Glyburide.

Plasma: Male Sprague-Dawley rat plasma (with sodium heparin), purchased from Bioreclamation LLC (Liverpool, N.Y.).

Whole blood: Male Sprague Dawley whole blood (with sodium heparin), purchased from Bioreclamation LLC (Liverpool, N.Y.)

Lung homogenate: Male rat Sprague Dawley lung was purchased from Bioreclamation LLC (Liverpool, N.Y.). The lung was homogenized using polytron homogenizer after addition of 5× volume of 1×PBS. The homogenate was centrifuged at 9000 rpm for 10 min at 4° C. The supernatant was centrifuged again at 3000 rpm for 30 min to make a clear supernatant. Protein concentration was determined using a commercial kit (Pierce, Thermo Scientific).

Sample Preparation Procedure: (Peptides)

Test article was prepared in one of the following biological matrices: heparinized rat plasma, heparinized rat whole blood or lung homogenate. The plasma and whole blood sample was prepared at 5000 ng/mL by adding 5 uL of 1 mg/mL Working solution to 995 uL of rat plasma or whole blood. Lung homogenate samples were prepared by diluting lung homogenate to 1 mg/ml protein concentration with phosphate buffered saline (PBS), followed by addition of 5 uL Working solution to 995 uL diluted lung homogenate. The samples were incubated at 37° C. with gentle shaking (65~75 rpm) in a water bath incubator. At times 0 min, 5 min, 15 min, 30 min, 60 min, 120 and 240 min, 25 uL aliquots of incubation samples were transferred to 96-well plate and immediately protein precipitated using 150 uL of Extraction solution. After completion of incubation experiment, the sample plate was centrifuged at 4000 rpm at 4° C. for 10 minutes. Afterwards, a pipetting device (Tecan Temo) was used to transfer the supernatants to another plate and add 50 uL of water to all samples. The plate was vortexed prior to LC-MS analysis.

Sample Preparation Procedure (Conjugates)

Test article was prepared at 50,000 ng/mL by adding 5 uL of 1 mg/mL Working solution to 495 uL of rat plasma. The samples were incubated at 37° C. with gentle shaking (65-75 rpm) in a water bath incubator. At times 0 hr, 0.5 hr, 1 hr, 2 hr, 4 hr, 6 and 24 hr, 50 uL aliquots of incubation samples were transferred to 96-well plate and 100 uL 40 mM TCEP (tris(2-carboxyethyl)phosphine) was added to each sample. The reaction mixture was incubated at 37° C. for 1 hour. After completion of reaction, protein precipitation was performed using 300 uL of acetonitrile. The sample plate was centrifuged at 4000 rpm at 4° C. for 10 minutes. Afterwards, a pipetting device (Tecan Temo) was used to transfer 125 uL supernatants to another plate and adds 50 uL of water to all samples. The plate was vortexed prior to LC-MS analysis.

LC-MS Analysis of Stability Samples

HPLC: Agilent 1290 HPLC with autosampler

Column: MAC-MOD ACE C18, 3 μm, 30 mm×2.1 mm i.d.

Mobile phase A: 0.1% Formic acid in acetonitrile

Mobile phase B: 0.1% Formic acid in water

Gradient Program:

| Time (min) | Flow (mL) | Mobile Phase A(%) | Mobile Phase B(%) |
|---|---|---|---|
| 0 | 0.4 | 95 | 5 |
| 0.5 | 0.4 | 95 | 5 |
| 1.5 | 0.4 | 5 | 95 |
| 4.1 | 0.4 | 5 | 95 |
| 4.2 | 0.4 | 95 | 5 |
| 5 | 0.4 | 95 | 5 |

Mass spectrometer: Agilent Q-TOF 6530

Data acquisition mode: Full scan with mass range of 100-1000 m/z

Data acquisition and analysis software: MassHunter

Data Analysis:

Stability assay: stability half-life, (t ½), values were determined by converting peak areas at each time point to percent remaining relative to initial (t=0) peak area.

Percent remaining=100× (sample peak area)÷ (t=0 peak area)

The natural log of percent remaining values were calculated and plotted against sample time (Microsoft Excel). The slope of this line, k, was determined by linear regression (Microsoft Excel).

Stability half-life was then calculated by the formula, t½=0.693÷k

Surrogate Activity-Based Plasma Stability Assay:

The calcium flux protocol described above was followed, with the following changes. The peptides were also incubated with 5% rat plasma (Bioreclamation # RATPLNAHP-M, Na Heparin-treated). Readings were taken at time points $t_0$ and $t_{24\ hrs}$, after incubation in a 37° C. tissue culture incubator. Peptide plasma half-life in minutes was estimated by calculating the following:

1) $LN((EC_{50}\ at\ t_0)/(EC_{50}\ at\ t_{24\ hrs}))$,
2) Calculate slope of value above and
3) $t_{1/2}=0.693/(slope^2)$.

TABLE 1

Activity and Stability of Conjugates

| Bioconjugate | hAPJ $Ca^{2+}$ Flux $EC_{50}$ [nM] | Surrogate activity-based Plasma stability $t\frac{1}{2}$ [min] |
|---|---|---|
| Example 1 | 111.2 | >1000 |
| Example 2 | 84.8 | >1000 |
| Example 3 | 115.1 | >1000 |
| Example 4 | 157.9 | >1000 |
| pE-R-P-R-L-C*-H-K-G-P-Nle-C*-F-OH (non-conjugated cyclic peptide- Example 8 of WO2013/111110 | 1.0 | 132 |
| Comparative Example: Pyr-1-Apelin-13 | 6.6 | 5.0 |

TABLE 2

Correlation bewteen plasma stabililty Assay and Surrogate Activity based Plasma Stability assay:

| Conjugate | Plasma stability $t\frac{1}{2}$ [min] | Surrogate Activity based Plasma stability $t\frac{1}{2}$ [min] |
|---|---|---|
| Pyr-1-Apelin 13 | 6.6 | 5.0 |
| pE-R-P-R-L-C*-H-K-G-P-Nle-C*-F-OH (non-fused cyclic analog- Example 8 of WO2013/111110 | 163 | 132 |

Protocols and Data for the In Vivo Pharmacokinetic Assessment Via SC Dosing.
Formulation, Dosing and Sample Acquisition:

Example 1 and example 4 were dissolved to 0.1 mg/ml concentration in 30% (w/v) PEG300 and 5% (w/v) dextrose in PBS. C57/B6 mice (~20 weeks of age) were dosed with dissolved compound by subcutaneous (SC) injection into the flank (n=4 per compound). Injection volume was 10 ml/kg. Blood samples were withdrawn from the saphenous vein at 3 and 6 hours post-dose, as well as at 1, 2, 4, 7 and 10 days post dose. Blood samples were immediately centrifuged at 4000×g for 10 min. Plasma supernatant (10 µL) was transferred to a 96-well plate and frozen at −80 C until analysis.

Example 8 of WO2013/111110 was dissolved in sterile water for injection (Hospira) to 1 mg/ml concentration. C57/B6J mice (~22 weeks of age) were dosed with dissolved compound by SC injection (n=4). Blood samples were withdrawn from the tail vein at 15, 30, 60 and 120 minutes post injection. These were immediately centrifuged and then plasma supernatant was transferred to a 96-well plate and frozen at −80 C until analysis.

Preparation of Samples for Bioanalysis:

A pre-weighed sample of each compound (1-3 mg) was obtained and dissolved to 1 mg/ml in DMSO. These were diluted serially in mouse plasma (BioReclamation) to final concentrations of 10,000, 5,000, 1,000, 500, 100, 50, 10, 5, and 1 ng/ml to make standard curve for analysis.

Plasma samples from PK studies were thawed and diluted to 25 µL total volume by addition of mouse plasma.

25 µL aliquots of each sample and standard curve sample were arranged on a 96-well plate.

150 µL acetonitrile containing 100 ng/ml glyburide as internal standard was added to each sample and the samples vortexed for 30 seconds. Samples were then centrifuged at 4000×g for 10 minutes. 125 µL supernatant was then transferred to a fresh 96-well plate. 50 µL of water was added and mixed by vortexing for 30 seconds.

LC/MS Bioanalysis (Agilent 1290):

Samples (10 µL) were transferred to an HPLC using a CTC PAL autosampler. The LC column was ACE C18 30×2.1 mm, 3.0 µm bead. A binary solvent system with Solvent A consisting of 0.1% Formic acid in water and Solvent B consisting of 0.1% Formic acid in acetonitrile was used. Samples were loaded onto the column in 95% Solvent A (0-0.5 min) and eluted by a gradient of 5% to 50% Solvent B (0.5 to 1.8 min) and 50% to 98% Solvent B over 1.8 to 2.3 min. Column was held at 98% Solvent B from 2.3 to 2.9 min and returned to 95% Solvent A over 2.9-3.0 min with equilibration of column with 95% Solvent A from 3.0-3.5 min. Solvent flow rate was 700 µL/min and column temperature 50 C.

Results: The mouse plasma exposure profiles of compounds of examples 1 and 4 following s.c. dosing are shown in FIG. 1; and half-lives are summarized in table 3;

TABLE 3

| Compound | $t\frac{1}{2}$ [h] |
|---|---|
| Example 1 | 43 |
| Example 4 | 23 |
| pE-R-P-R-L-C*-H-K-G-P-Nle-C*-F-OH (non-fused cyclic analog- Example 8 of WO2013/111110 | 0.52 |

The conjugate of the present invention may have an APJ receptor potency similar to apelin-13 or pyr-1-apelin-13. In one embodiment the bioconjugate of the present invention has an $EC_{50}$ of less than 400 nM. In another embodiment the apelin fatty acid conjugates of the invention has an $EC_{50}$ of less than 300 nM, preferably less than 200 nM and more preferably less than 160 nM. In yet another embodiment, the bioconjugate of the present invention has an $EC_{50}$ of less than 100 nM.

The conjugate of the present invention have plasma stability superior to apelin-13 or pyr-1-apelin-13 and/or superior to the unconjugated analog Q-R-P-R-L-C*-H-K-G-P-(Nle)-C*-F (or pE-R-P-R-L-C*-H-K-G-P-Nle-C*-F-OH) and/or superior to previously described apelin-fatty acid conjugate (Example 20 of U.S. patent application Ser. No. 14/336,290. In one embodiment, the plasma stability improvement is at least 2 fold. In another embodiment, the plasma stability improvement is at least 10 fold. In one embodiment, the bioconjugate of the invention has a plasma stability of at least 30 minutes or at least 60 minutes. In another embodiment, the fatty acid conjugate of the invention has a plasma stability of at least 5 h, preferably at least 10 h and more preferably at least 12 h.

The conjugate of the present invention may be administered either simultaneously with, or before or after, one or more other therapeutic agent. The conjugate of the present invention may be administered separately, by the same or different route of administration, or together in the same pharmaceutical composition as the other agents.

In one embodiment, the invention provides a product comprising a conjugate of anyone of embodiments 1 to 7D, or a pharmaceutically acceptable salt thereof, and at least one other therapeutic agent as a combined preparation for simultaneous, separate or sequential use in therapy. In one embodiment, the therapy is the treatment of a disease or condition responsive to the activation of the APJ receptor.

Products provided as a combined preparation include a composition comprising a conjugate of anyone of embodiments 1 to 7D, or a pharmaceutically acceptable salt thereof, and the other therapeutic agent(s) together in the same pharmaceutical composition, or a conjugate of anyone of embodiments 1 to 7D, or a pharmaceutically acceptable salt thereof, and the other therapeutic agent(s) in separate form, e.g. in the form of a kit.

In one embodiment, the invention provides a pharmaceutical composition comprising a conjugate of anyone of embodiments 1 to 7D, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a conjugate according to anyone of embodiments 1 to 7D, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the conjugate of the invention and the other therapeutic agent may be manufactured and/or formulated by the same or different manufacturers. Moreover, the conjugate of the invention and the other therapeutic may be brought together into a combination therapy: (i) prior to release of the combination product to physicians (e.g. in the case of a kit comprising the conjugate of the invention and the other therapeutic agent); (ii) by the physician themselves (or under the guidance of the physician) shortly before administration; (iii) in the patient themselves, e.g. during sequential administration of a conjugate of the invention and the other therapeutic agent.

Accordingly, the invention provides the use of a conjugate according to anyone of embodiments 1 to 7D, or a pharmaceutically acceptable salt thereof, for treating a disease or condition responsive to the agonism of the APJ receptor, wherein the medicament is prepared for administration with another therapeutic agent. The invention also provides the use of another therapeutic agent for treating a disease or condition responsive to the agonism of the apelin receptor, wherein the medicament is administered with a conjugate according to anyone of embodiments 1 to 7D, or a pharmaceutically acceptable salt thereof.

The invention also provides a conjugate according to anyone of embodiments 1 to 7 for use in a method of treating a disease or condition responsive to the agonism of the APJ receptor, wherein the conjugate is prepared for administration with another therapeutic agent. The invention also provides another therapeutic agent for use in a method of treating a disease or condition responsive to the agonism of the APJ receptor, wherein the other therapeutic agent is prepared for administration with a conjugate according to anyone of embodiments 1 to 7D, or a pharmaceutically acceptable salt thereof.

The invention also provides the use of a conjugate according to anyone of embodiments 1 to 7D, or a pharmaceutically acceptable salt thereof, for treating a disease or condition responsive to the agonism of the APJ receptor, wherein the patient has previously (e.g. within 24 hours) been treated with another therapeutic agent. The invention also provides the use of another therapeutic agent for treating a disease or condition responsive to the agonism of the APJ receptor, wherein the patient has previously (e.g. within 24 hours) been treated with a conjugate according to anyone of embodiments 1 to 7D, or a pharmaceutically acceptable salt thereof.

In one embodiment, the other therapeutic agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

The term "in combination with" a second agent or treatment includes co-administration of the conjugate of the invention (e.g., a conjugate according to anyone of embodiments 1 to 7D, or a pharmaceutically acceptable salt thereof, or a conjugate otherwise described herein) with the second agent or treatment, administration of the compound of the invention first, followed by the second agent or treatment and administration of the second agent or treatment first, followed by the conjugate of the invention.

The term "second agent" includes any agent which is known in the art to treat, prevent, or reduce the symptoms of a disease or disorder described herein, e.g. a disorder or disease responsive to the activation of the APJ receptor, such as for example, acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

Examples of second agents include inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and/or a NEP inhibitor.

Inotropes as used herein include for example dobutamine, isoproterenol, milrinone, amirinone, levosimendan, epinephrine, norepinephrine, isoproterenol and digoxin.

Beta adrenergic receptor blockers as used herein include for example acebutolol, atenolol, betaxolol, bisoprolol, carteolol, metoprolol, nadolol, propranolol, sotalol and timolol.

Anti-coagulants as used herein include Dalteparin, Danaparoid, Enoxaparin, Heparin, Tinzaparin, Warfarin.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rosuvastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moexipril, moveltopril, perindopril, quinapril, ramipril, spirapril, temocapril, and trandolapril, or, pharmaceutically acceptable salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1 S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R—(R*, S*)]—N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy) phenyl]methyl}-8-methyl-2-(propan-2-yl)nonanamide) and zankiren (chemical name: [1 S-[1R*[R*(R*)],2S*, 3R*]]—N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

(A)
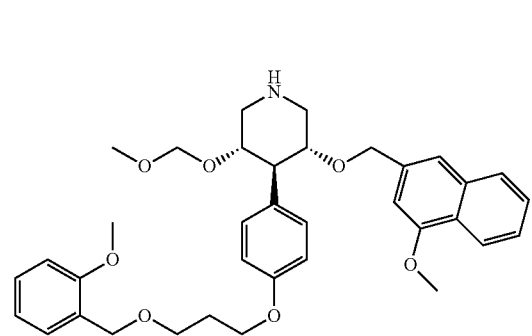

and (B)
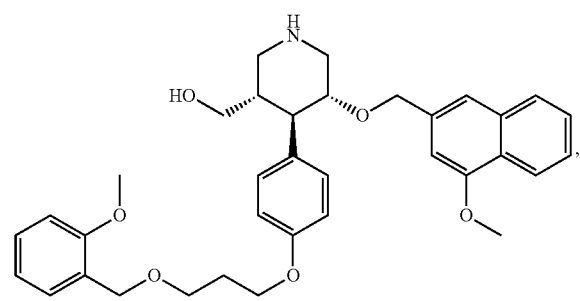

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

The term "calcium channel blocker (CCB)" includes dihydropyridines (DHPs) and non-DHPs (e.g., diltiazem-type and verapamil-type CCBs). Examples include amlodipine, Bepridil, Diltiazem, felodipine, ryosidine, isradipine, lacidipine, nicardipine, nifedipine, niguldipine, niludipine, nimodipine, nisoldipine, nitrendipine, Verapamil and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

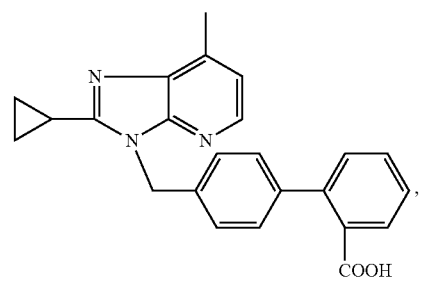 [SMILES: Cc1ccnc2c1nc(C1CC1)n2Cc1ccc(-c2ccccc2C(=O)O)cc1]

the compound with the designation SC-52458 of the following formula

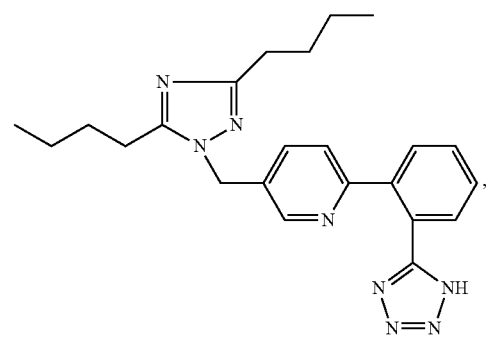 [SMILES: CCCCc1nc(CCCC)n(Cc2ccc(-c3ccccc3-c3nnn[nH]3)nc2)n1]

and the compound with the designation ZD-8731 of the following formula

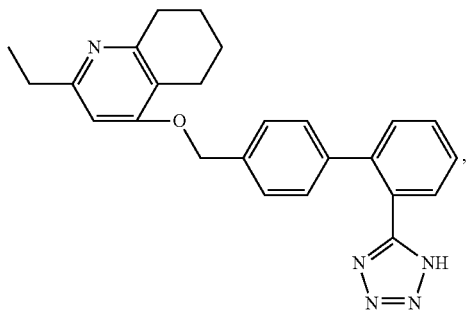 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are candesartan, eprosartan, irbesartan, losartan, telmisartan, valsartan. Also preferred are those agents which have been marketed, most preferred is valsartan or a pharmaceutically acceptable salt thereof.

The term "anti-diabetic agent" includes insulin secretion enhancers that promote the secretion of insulin from pancreatic □-cells. Examples include biguanide derivatives (e.g., metformin), sulfonylureas (SU) (e.g., tolbutamide, chlorpropamide, tolazamide, acetohexamide, 4-chloro-N-[(1-pyrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

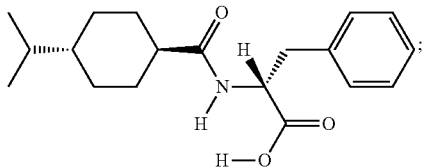 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058).

Further examples of second agents with which the conjugate of the invention can be used in combination include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV (dipeptidyl peptidase IV) inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 (glucagon like peptide-1) is an insulinotropic protein which is described, e.g., by W. E. Schmidt et al. in Diabetologia, 28, 1985, 704-707 and in U.S. Pat. No. 5,705,483.

The term "GLP-1 agonists" includes variants and analogs of GLP-1(7-36)$NH_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1 (7-37), $LYS^{18}$-GLP-1(7-37) and, in particular, GLP-1(7-37) OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl] methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl]-2-propynyl]-5-phenylsulfonyl)thiazolidine-2,4-dione, 5-[3-(4-chlorophenyl]-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγagonists; dual PPARα/PPARγagonists; antidiabetic vanadium containing compounds; incretin hormones, like glucagon-like peptide-1 (GLP-1) and GLP-1 agonists; beta-cell imidazoline receptor antagonists; miglitol; $\alpha_2$-adrenergic antagonists; and pharmaceutically acceptable salts thereof.

In one embodiment, the invention provides a combination, in particular a pharmaceutical combination, comprising a therapeutically effective amount of the conjugate according to anyone of embodiments 1 to 7D, or a pharmaceutically acceptable salt thereof, and one or more therapeutically active agents selected from β-adrenergic receptor blockers such as acebutolol, atenolol, betaxolol, bisoprolol, metoprolol, nadolol, propranolol, sotalol and timolol; angiotensin II receptor antagonists such as AT1 blockers; antidiabetic agents such as DPPIV inhibitors (e.g. vildagliptin) and GLP1 peptide agonist.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. An example of non-steroidal aldosterone synthase inhibitor is the (+)-enantiomer of the hydrochloride of fadrozole (U.S. Pat. Nos. 4,617,307 and 4,889,861) of formula

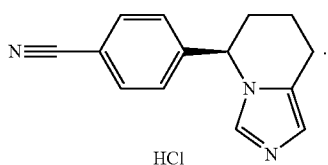 [SMILES: N#Cc1ccc([C@H]2CCCc3cncn32)cc1 ; Cl]

or, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methyl-benzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluorobenzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c1[1, 4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl) benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl 1-5,6-dihydro-8H-imidazo[5,1-c][1,4] oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g. in WO 2009/156462 and WO 2010/130796, in particular in the compound claims and the final products of the working examples, the subject-matter of the final products, the pharmaceutical preparations and the claims. Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl)ethanesulfonamide, N-((5-(3-chloro-4-cyanophenyl)pyridin-3-yl)(cyclopropyl)methyl)ethanesulfonamide, N-(cyclopropyl (5-(1H-indol-5-yl)pyridin-3-yl)methyl)ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan and ambrisentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.*; 6:1951-1954 (1996), respectively. Furthermore, the CETP inhibitors also include those disclosed in WO2000/017165, WO2005/095409, WO2005/097806, WO 2007/128568, WO2008/009435, WO 2009/059943 and WO2009/071509.

The term "NEP inhibitor" refers to a compound that inhibits neutral endopeptidase (NEP) EC 3.4.24.11. Examples include Candoxatril, Candoxatrilat, Dexecadotril, Ecadotril, Racecadotril, Sampatrilat, Fasidotril, Omapatrilat, Gemopatrilat, Daglutril, SCH-42495, SCH-32615, UK-447841, AVE-0848, PL-37 and (2R,4S)-5-Biphenyl-4-yl-4-(3-carboxy-propionylamino)-2-methyl-pentanoic acid ethyl ester or a pharmaceutically acceptable salt thereof. NEP inhibitors also include Phosphono/biaryl substituted dipeptide derivatives, as disclosed in U.S. Pat. No. 5,155, 100. NEP inhibitors also include N-mercaptoacyl phenylalanine derivative as disclosed in PCT application Number WO 2003/104200. NEP inhibitors also include dual-acting antihypertensive agents as disclosed in PCT application Numbers WO 2008/133896, WO 2009/035543 or WO 2009/134741. Other examples include compounds disclosed in U.S. application Ser. Nos. 12/788,794; 12/788,766 and 12/947,029. NEP inhibitors also include compounds disclosed in WO 2010/136474, WO 2010/136493, WO 2011/061271 and U.S. provisional applications Nos. 61/414,171 and 61/414,163.

In one embodiment, the invention provides a method of activating the APJ receptor in a subject, wherein the method comprises administering to the subject a therapeutically effective amount of the conjugate according to anyone of the preceding embodiments, or a pharmaceutically acceptable salt thereof.

In one embodiment, the invention provides a method of treating a disorder or a disease responsive to the activation of the APJ receptor, in a subject, wherein the method comprises administering to the subject a therapeutically effective amount of conjugate according to anyone of the preceding embodiments, or a pharmaceutically acceptable salt thereof.

In one embodiment, the invention provides a method of treating a disorder or a disease responsive to the activation (agonism) of the APJ receptor, in a subject, wherein the disorder or the disease is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

In one embodiment, the invention provides a conjugate according to anyone of the preceding embodiments, or a pharmaceutically acceptable salt thereof, for use as a medicament.

In one embodiment, the invention provides the use of a conjugate according to anyone of the preceding embodiments, or a pharmaceutically acceptable salt thereof, in the manufacture of a medicament, for the treatment of a disorder or disease responsive to the activation of the APJ receptor. In another embodiment, the invention provides the use of a conjugate according to anyone of the preceding embodiments, or a pharmaceutically acceptable salt thereof, in the manufacture of a medicament, for the treatment of a disorder or disease responsive to the activation of the APJ receptor, wherein said disorder or disease is in particular selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

EXEMPLIFICATION OF THE INVENTION

| Abbreviation | Definition |
|---|---|
| AA | Amino acid |
| Ac | Acetyl |
| ACN | Acetonitrile |
| AcOH | Acetic acid |
| BSA | Bovine Serum Albumin |
| Boc | tert-Butyloxycarbonyl |
| CAD | Charged aerosol detector |
| DCC | Dicyclohexyl Carbodiimide |
| DCM | Dichloromethane |
| DIPEA or DIEA | N,N'-Diisopropylethylamine |
| DMF | N,N'-Dimethylformamide |
| DTT | Dithiothreitol |
| ELSD | Evaporative light scattering detector |
| EtOAc | Ethyl Acetate |
| FA | Fatty acid |
| Fmoc | 9-Fluorenylmethyloxycarbonyl |
| HATU | 2-(1H-9-Azabenzotriazole-1-yl)-1,1,3,3-tetramethyluronium hexafluorophosphate |
| HBSS | Hank's buffered salt solution |
| HCTU | 2-(6-Chloro-1H-Benzotriazole-yl)-1,1,3,3-tetramethyluronium hexafluorophosphate |
| HEP | Heptane |
| HEPES | 4-(2-hydroxyethyl)-1-piperazineethanesulfonic acid |
| HFIP | Hexafluoroisopropanol |
| HPLC | High performance liquid chromatography |
| LCMS | Liquid Chromatography Mass Spectroscopy |
| LN | Logarithmus naturali (natural logarithm) |
| MeOH | Methanol |
| MS | Mass spectrometry |
| Nle | Norleucine |
| NMR | Nuclear Magnetic Resonance |
| Oxyma Pure | Ethyl 2-cyano-2-(hydroxyimino)acetate |
| Pbf | 2,2,4,6,7-Pentamethyldihydrobenzofuran-5-sulfonyl |
| pE | Pyroglutamate |
| PEG | Polyethylene glycol |
| PG | Protecting group |
| Pbf | Pentamethyl-dihydrobenzofuran-5-sulfonyl |
| PBS | Phosphate buffered saline |
| Ph | Phenyl |
| PS | Polystyrene |
| POL | Polymer support |
| rt | Room temperature |
| SPPS | Solid phase peptide synthesis |
| TCEP | Tris(2-carboxyethyl)phosphine |
| TFA | Trifluoroacetic acid |
| THF | Tetrahydrofuran |
| TIPS | Triisopropylsilane |
| $t_R$ | Retention time |
| Trt | Trityl |
| UPLC | Ultra performance liquid chromatography |
| UV | Ultraviolet |

Methods
Analytical Method A:
    Acquity BEH 1.7 µm 2.1×50 mm
    Eluent: A: Water (0.1% formic acid); B: ACN (0.1% formic acid)
    Flow rate: 1 mL/min
    Gradient: 0 min 2% B; 2% to 98% B in 1.76 min; 2.06 min 98% B; 2.16 min 2% B
    Mass Spectrometer: Single Quadrupole ESI scan range 120-1600
    HPLC: waters Acquity
    Temperature: 50 C
Analytical Method B:
    Acquity BEH 1.7 µm 2.1×50 mm
    Eluent: A: Water (0.1% formic acid); B: ACN (0.1% formic acid)
    Flow rate: 1 mL/min
    Gradient: 0 min 40% B; 40% to 98% B in 1.40 min; 2.05 min 98% B; 2.1 min 40% B
    Mass Spectrometer: Single Quadrupole ESI scan range 120-1600
    HPLC: waters Acquity
    Temperature: 50 C
Analytical Method C:
    Hilic 2.1×100 mm
    Eluent: A: $CO_2$ B: MeOH
    Flow rate: 2 mL/min
    Gradient: 0.15 min 2% B; 2% to 50% B in 1.65 min; 2.1 min 50% B; 2.25 min 2% B; 2.5 min 2% B
    Mass Spectrometer: Single Quadrupole ESI
    SCF: waters Acquity
    Temperature: 55 C
Analytical Method D:
    Sunfire C18 3.5 µm 3.0×3.0 mm
    Eluent: A: Water (0.05% Trifluoroacetic acid); B: ACN
    Flow rate: 2 mL/min
    Gradient: 0 min 5% B; 5% to 80% B in 4.3 min; 4.70 min 95% B; 5.00 min 95% B; 5.10 min 5% B
    Mass Spectrometer: Waters micromass ZQ; Single Quadrupole ESI scan range 120-1600
    HPLC: Agilent 1100 series
    Temperature: 40 C
Analytical Method E:
    Xbridge C18 Column, 3.5 µM, 3.0×3.0 mm
    Eluent: A: Water+5 mM Ammonium Hydroxide B: ACN
    Flow rate: 2 mL/min
    Gradient: 0.0 min 2% B; 2% to 95% B in 1.70 min; 2.00 min 95% B; 2.10 min 5% B;
    Mass Spectrometer: Single Quadrupole ESI
    HPLC: Agilent 1100 series
    Temperature: 40 C Preparation of Fatty Acid-Linker Construct #1

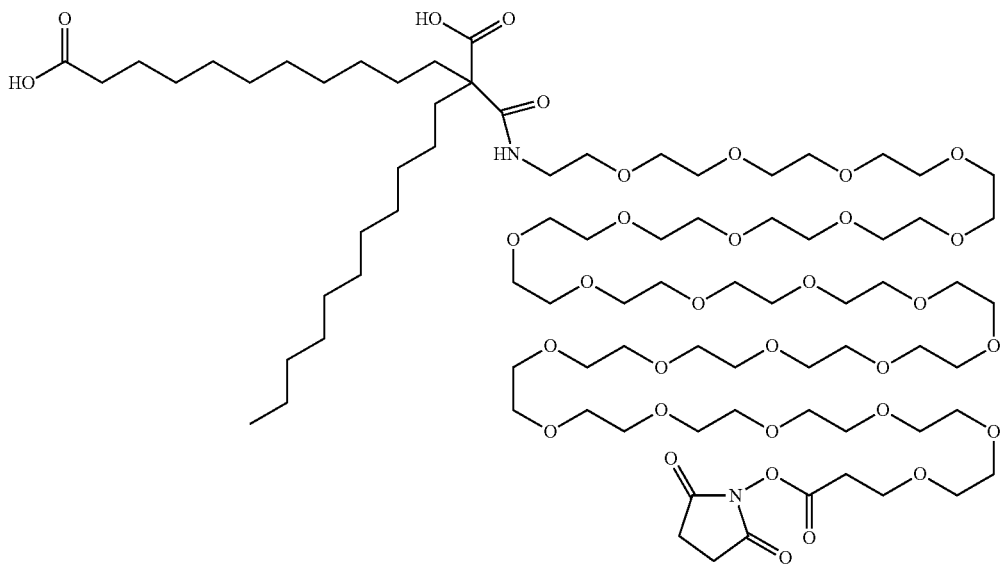 [SMILES: CCCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCOCCC(=O)ON1C(=O)CCC1=O]

Step 1: 1-Benzyl 3-tert-butyl 2-undecylmalonate

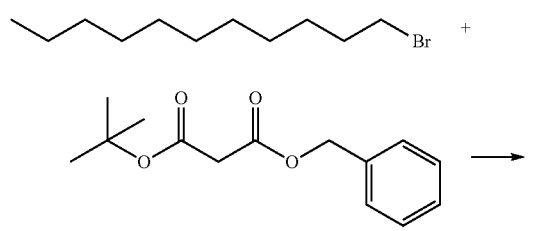

To a suspension of NaH (160 mg, 4.0 mmol) in DMF (8 mL) at 0° C. under $N_2$, was added benzyl tert-butyl malonate (1.0 g, 4.0 mmol) in DMF (2 mL). The mixture was stirred for 50 min after which 1-bromoundecane in DMF (2 mL) was added. After an additional hour of stirring the reaction was allowed to warm to room temperature. The reaction was maintained overnight. $Et_2O$ (100 mL) and water (20 mL) were added to partition the reaction. The aqueous phase was extracted with $Et_2O$ (100 mL), and the combined organics dried over $Na_2SO_4$. The solvent was evaporated and the residue purified by flash column (C18 12 g, 40-100% ACN/water+0.1% TFA) to yield the title compound as a colorless oil (1.14 g, 2.82 mmol, 71%): LCMS Method B Rt=1.58 min, M+Na 427.4; $^1$H NMR (400 MHz, CHLOROFORM-d) δ ppm 0.84-0.96 (m, 3 H) 1.28 (br. s, 12 H) 1.31 (m, J=3.90 Hz, 6 H) 1.41 (s, 9 H) 1.88 (q, J=7.38 Hz, 2 H) 3.29 (t, J=7.58 Hz, 1 H) 5.19 (q, J=12.27 Hz, 2 H) 7.30-7.42 (m, 5 H).

Step 2: 1,11-Dibenzyl 11-Tert-Butyl Docosane-1,11,11-Tricarboxylate

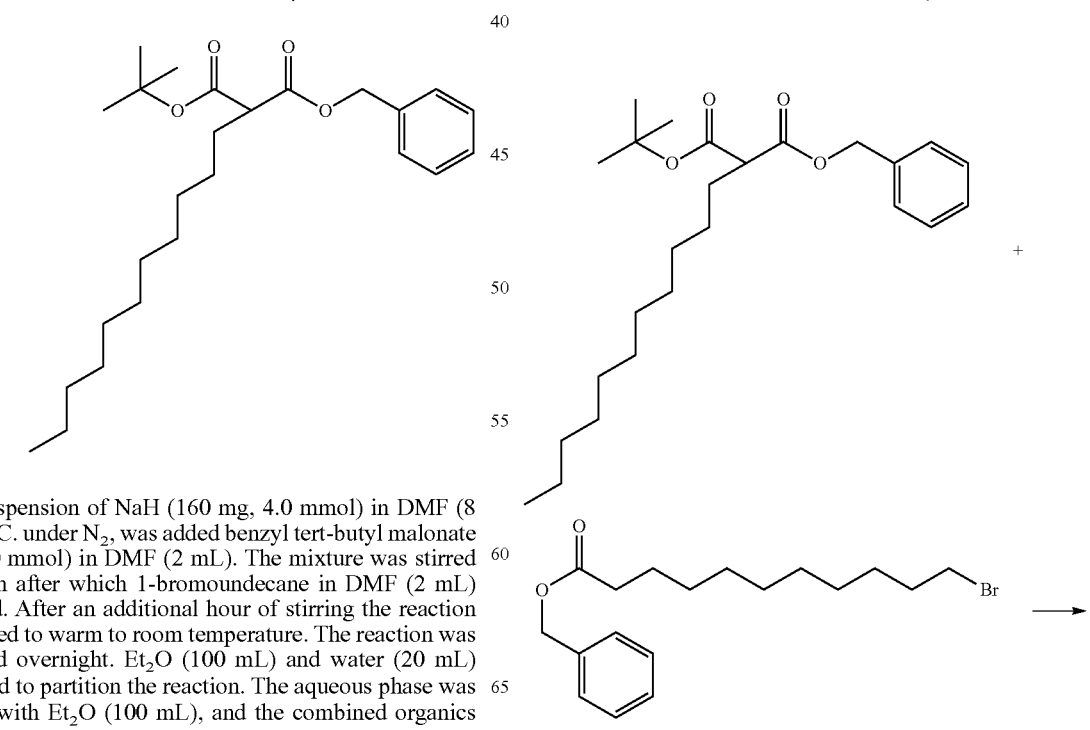

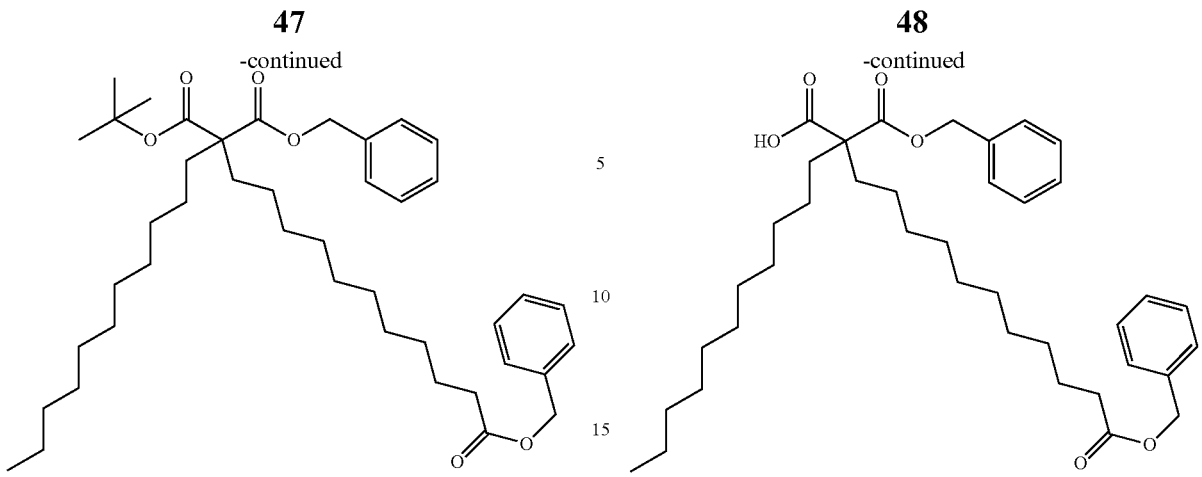

A solution of 1-Benzyl 3-tert-butyl 2-undecylmalonate (650 mg, 1.61 mmol) in DMF (1 mL) was slowly added to a suspension of NaH (70.7 mg, 1.77 mmoL) in DMF (6 mL) at 0° C. under $N_2$. The mixture was stirred for 40 min before the addition of benzyl 11-bromoundecanoate (571 mg, 1.61 mmol) in DMF (1 mL). Upon addition the reaction was allowed to warm to room temperature and stirred overnight. The reaction was diluted with $Et_2O$ (100 mL) and extracted with water (20 mL). The aqueous phase was extracted with $Et_2O$ (100 mL), and the combined organics dried over $Na_2SO_4$. The solvent was evaporated. The residue was purified by flash column (silica 80 g, 0-10% EtOAc/HEP) to yield the titled compound as a colorless oil (823 mg, 1.21 mmol, 75%): $^1$H NMR (400 MHz, CHLOROFORM-d) δ ppm 0.84-0.94 (m, 3 H) 1.12 (m, J=6.60 Hz, 4 H) 1.19-1.33 (m, 28 H) 1.35 (s, 9 H) 1.66 (quin, J=7.40 Hz, 2 H) 1.85 (t, J=8.44 Hz, 4 H) 2.37 (t, J=7.52 Hz, 2 H) 5.14 (s, 2 H) 5.16 (s, 2 H) 7.30-7.42 (m, 10 H).

Step 3: 13-(Benzyloxy)-2-((benzyloxy)carbonyl)-13-oxo-2-undecyltridecanoic acid

To a solution of a compound from step 2 (200 mg, 0.295 mmol) in DCM (3 mL) was added TFA (0.6 mL), and the reaction stirred at room temperature for 3 hrs. The solvent was evaporated and the residue purified by flash column (silica 12 g, 0-15% EtOAc/HEP) to yield the title compound (177 mg, 0.284 mmol, 96%): $^1$H NMR (400 MHz, CHLOROFORM-d) δ ppm 0.87-0.94 (m, 3 H) 0.94-1.05 (m, 2 H) 1.19 (br. s., 14 H) 1.23-1.37 (m, 16 H) 1.65 (quin, J=7.40 Hz, 2 H) 1.78-1.91 (m, 2 H) 1.93-2.05 (m, 2 H) 2.37 (t, J=7.52 Hz, 2 H) 5.14 (s, 2 H) 5.27 (s, 2 H) 7.31-7.44 (m, 10 H).

Step 4: 1,11-Dibenzyl 11-(2,5-Dioxocyclopentyl) Docosane-1,11,11-Tricarboxylate

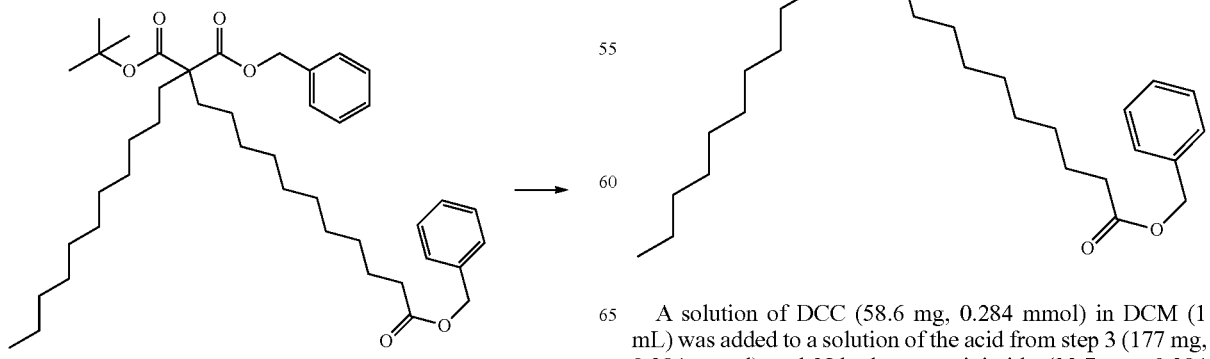

A solution of DCC (58.6 mg, 0.284 mmol) in DCM (1 mL) was added to a solution of the acid from step 3 (177 mg, 0.284 mmol) and N-hydroxysuccinimide (32.7 mg, 0.284 mmol) in DCM (2 mL) and THF (0.3 mL) under N₂. The reaction was stirred at room temperature for 4 hr. The solvent was evaporated and the residue purified by flash column (silica 12 g, 0-35% EtOAc/HEP) to yield the titled compound as a colorless oil (153 mg, 0.213 mmol, 75%): $^1$H NMR (400 MHz, CHLOROFORM-d) δ ppm 0.86-0.93 (m, 3 H) 1.12-1.21 (m, 2 H) 1.21-1.37 (m, 30 H) 1.66 (quin, J=7.40 Hz, 2 H) 1.89-2.07 (m, 4 H) 2.37 (t, J=7.58 Hz, 2 H) 2.84 (br. s., 4 H) 5.13 (s, 2 H) 5.25 (s, 2 H) 7.30-7.47 (m, 10 H).
Step 5
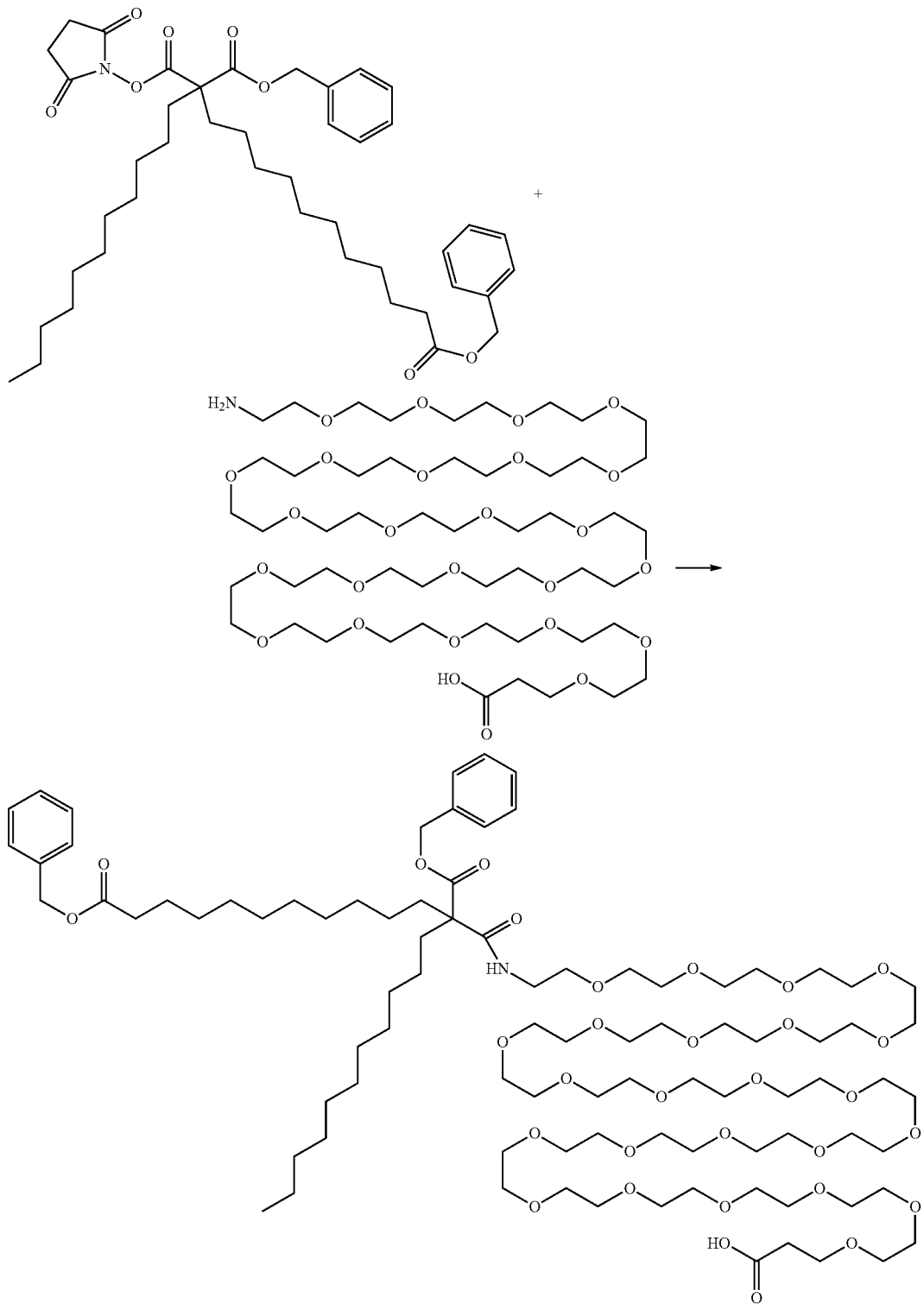

A solution of intermediate from step 4 (145 mg, 0.201 mmol) in THF (1.5 mL) and DCM (1.5 mL) was added to a vial charged with amino-PEG24-carboxylic acid. DIPEA (88 µL, 0.504 mmol) was added and the reaction agitated on a shaker plate for 15 hrs. The solvent was evaporated and the residue purified by supercritical fluid chromatography (Waters HILIC 20×150 mm; 15-25% MeOH/CO$_2$) to yield the desired coupled compound (151 mg, 0.086 mmol, 43%): LCMS Method C; Rt=1.30 min, [M+2H]+2 876.4; $^1$H NMR (400 MHz, CHLOROFORM-d) δ ppm 0.86-0.93 (m, 3 H) 0.93-1.04 (m, 2 H) 1.19 (br. s., 15 H) 1.23-1.37 (m, 15 H) 1.61-1.68 (m, 2 H) 1.78 (td, J=12.44, 4.34 Hz, 2 H) 1.92-2.05 (m, 2 H) 2.37 (t, J=7.58 Hz, 2 H) 2.62 (t, J=6.05 Hz, 2 H) 3.49 (dd, J=6.72, 2.32 Hz, 2 H) 3.52-3.59 (m, 2 H) 3.59-3.73 (m, 92 H) 3.80 (t, J=6.05 Hz, 2 H) 5.13 (s, 2 H) 5.18 (s, 2 H) 7.31-7.42 (m, 10 H) 8.09 (t, J=5.26 Hz, 1 H).

Step 6

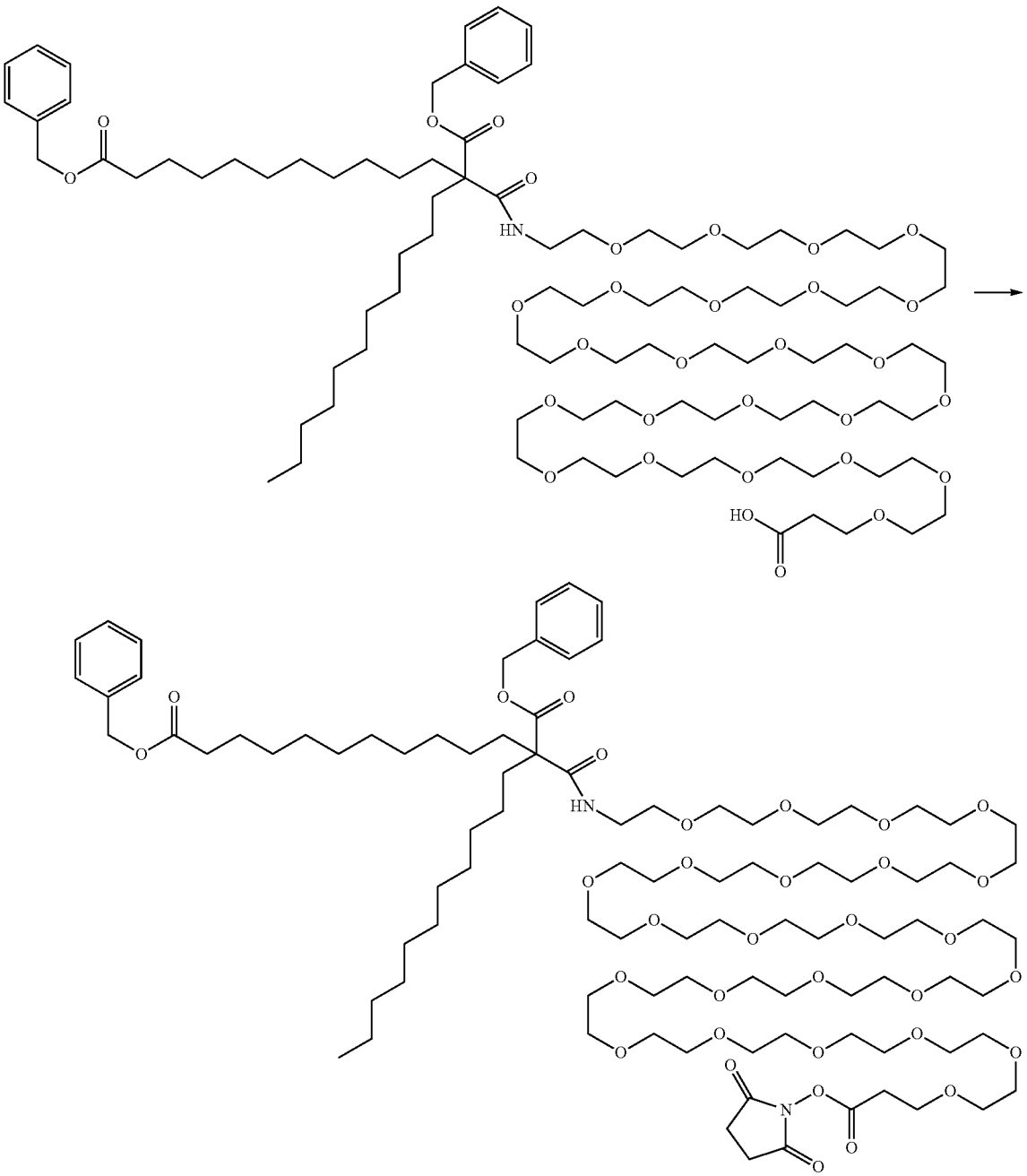

DCC (22 mg, 0.103 mmol) in DCM (0.265 mL) was added to a solution of compound from step 5 (150 mg, 0.086 mmol) and N-hydroxysuccinimide in DCM (1.5 mL). The reaction was stirred for 1.5 hrs. Additional N-hydroxysuccinimide (10 mg) in THF (0.5 mL) and DCC (22 mg) in DCM (0.265 mL) was added and the reaction stirred overnight. The solvent was evaporated and the residue purified by flash column (silica 12, 0-5% MeOH/DCM) to yield the activated NHS compound (159 mg, quantitative) as a white solid: LCMS Method B; Rt=1.55 min, [M+H$_3$O+H]$^{+2}$ 933.9.

Step 7

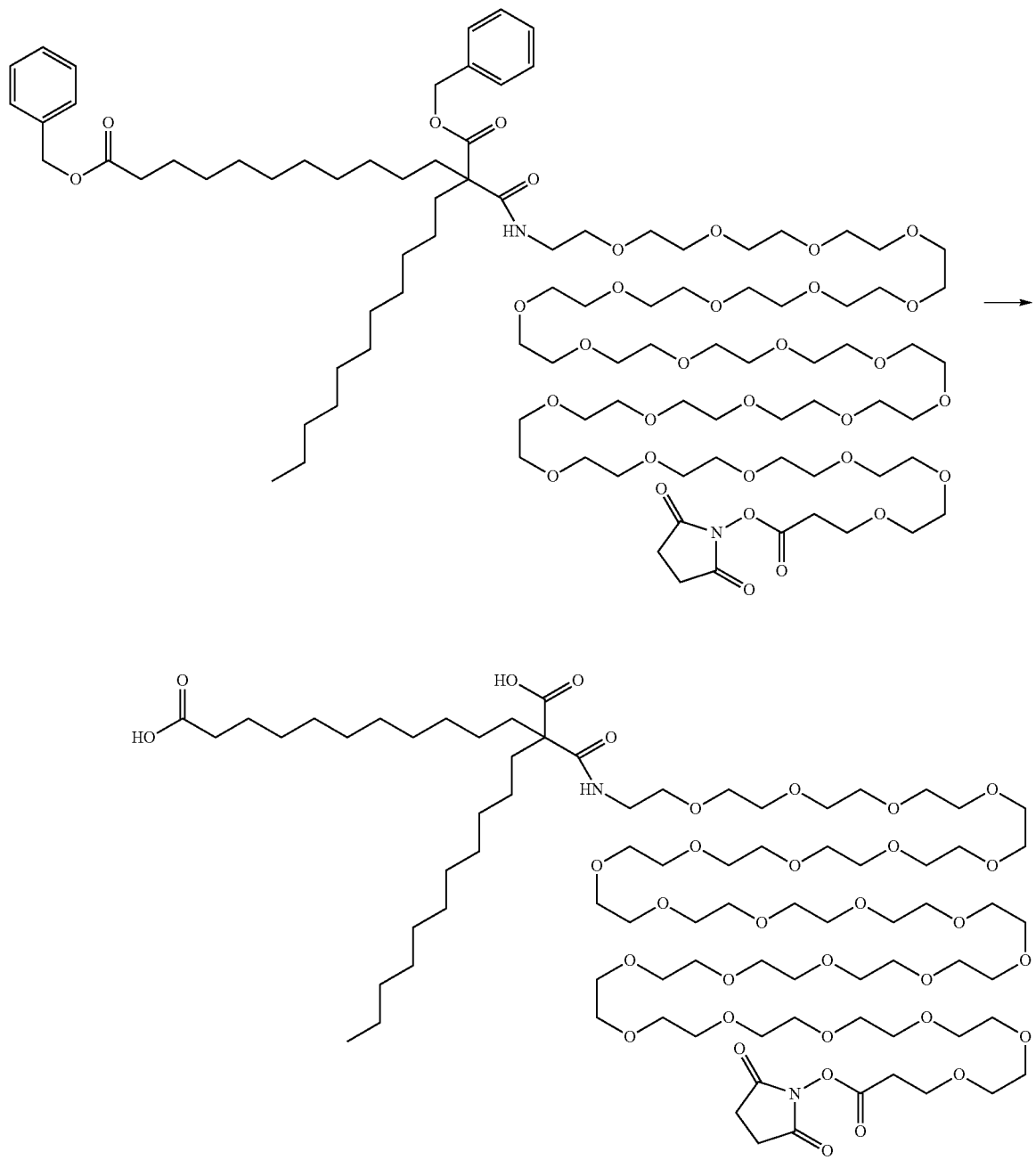 [SMILES: CCCCCCCCCCCC(CCCCCCCCCCC(=O)OCc1ccccc1)(C(=O)NCCOCCOCCOCCOCCOCCOCCOCCOCCOCCOCCOCCOCCOCCOCCOCCOCCOCCOCCOCCOCCOCCOCCOCCOCCC(=O)ON1C(=O)CCC1=O)C(=O)OCc1ccccc1 ; CCCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCOCCC(=O)ON1C(=O)CCC1=O]

To a solution of compound from step 6 (159 mg, 0.086 mmol) in THF (5 mL) was added a suspension of 10% Pd on carbon (4.6 mg, 4.3 μmol) in THF (1 mL). The reaction was placed under hydrogen and stirred for 40 min. More Pd on carbon (7 mg, 6.5 μmol) was added and the stirred another 1 hr under hydrogen. The reaction was passed through a membrane filter and the filtrate evaporated. The residue was purified by HPLC (Sunfire C18 30×50 mm, 45-70% ACN/water+0.1% TFA) to yield the deprotected compound (83 mg, 0.047 mmol, 54%): LCMS Method BRt=1.03 min, [M+2H]/2 835.2; $^1$H NMR (400 MHz, CHLOROFORM-d) δ ppm 0.84-0.94 (m, 3 H) 1.17 (br. s., 2 H) 1.21-1.39 (m, 30 H) 1.57-1.68 (m, 2 H) 1.69-1.80 (m, 2 H) 1.97-2.10 (m, 2 H) 2.34 (t, J=7.21 Hz, 2 H) 2.86 (s, 4 H) 2.92 (t, J=6.48 Hz, 2 H) 3.51-3.73 (m, 96 H) 3.87 (t, J=6.48 Hz, 2 H) 7.45 (t, J=4.46 Hz, 1 H).

The compounds of the following were prepared analogously to fatty acid-linker construct #1 by replacing Amino-PEG24-Carboxylic acid with the appropriate amino-PEGn-Carboxylic acid.

Preparation of Fatty Acid-Linker Construct #2

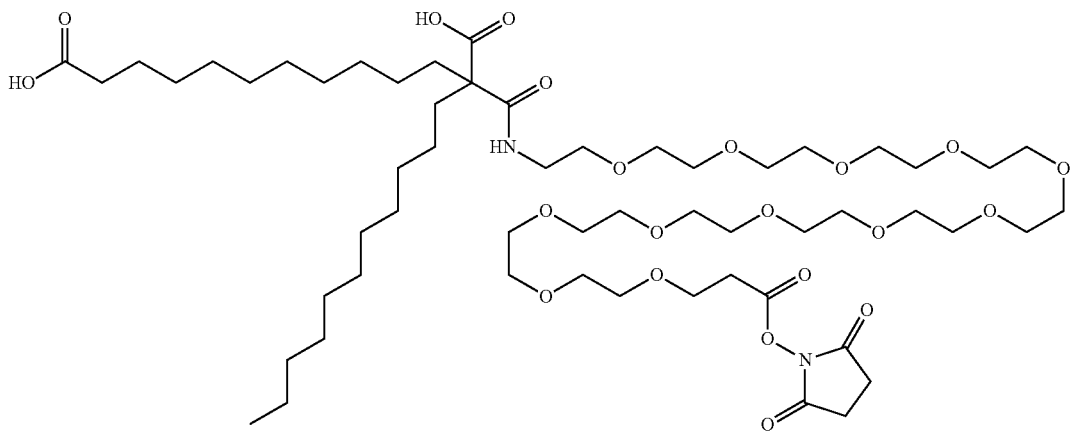 [SMILES: CCCCCCCCCCCC(CCCCCCCCCCC(=O)O)(C(=O)O)C(=O)NCCOCCOCCOCCOCCOCCOCCOCCOCCOCCOCCOCCOCCC(=O)ON1C(=O)CCC1=O]

Fatty acid-linker construct #2 was prepared using amino-PEG12-Carboxylic acid and was isolated as colorless oil;

LCMS: Method A: CAD: Rt 1.64 mins MS m/z 1138.0 [M−H]−;

1H NMR (400 MHz, CDCl3): δ 7.36 (1H, br t), 3.76 (2H, t), 3.61-3.47 (46H, br m), 3.46-3.40 (2H, br m), 2.81 (2H, t), 2.74 (4H, br s), 2.24 (2H. t), 1.93 (2H, br t), 1.68-1.57 (2H, br m), 1.56-1.50 (2H, br m), 1.26-1.08 (34H, br m), 0.78 (3H, t).

Preparation of Fatty Acid-Linker Construct #3

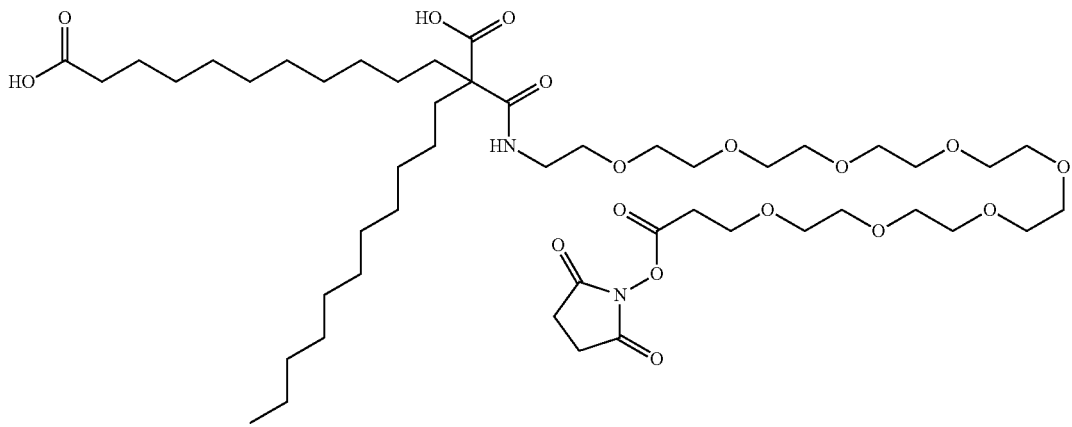 [SMILES: CCCCCCCCCCCC(CCCCCCCCCCC(=O)O)(C(=O)O)C(=O)NCCOCCOCCOCCOCCOCCOCCOCCOCCC(=O)ON1C(=O)CCC1=O]

The Fatty acid-linker construct #3 was prepared using amino-PEG8-Carboxylic acid and was isolated as 2 fractions, each of them having slightly different impurities and each of them being colorless oil.

LCMS: Method A CAD: Rt 1.65 mins MS m/z 963.8 [M+H]+;

1H NMR (400 MHz, CDCl3): δ 7.27 (1H, br m), 3.70 (2H, t), 3.56-3.41 (30H, br m), 3.41-3.34 (2H, br m), 2.75 (2H, t), 2.69 (4H, br s), 2.19 (2H. t), 1.87 (2H, br t), 1.63-1.52 (2H, br m), 1.52-1.43 (2H, br m), 1.22-1.02 (32H, br m), 0.78 (3H, t).

LCMS: Method B: CAD: Rt 1.65 mins MS m/z 963.8 [M+H]+;

1H NMR (400 MHz, CDCl3): δ 7.48 (1H, m), 3.85 (2H, t), 3.71-3.56 (30H, br m), 3.56-3.49 (2H, br m), 2.90 (2H, t), 2.84 (4H, br s), 2.38-2.32 (2H, m), 2.02 (2H, br t), 1.78-1.58 (4H, br m), 1.38-1.16 (32H, m), 0.88 (3H, t).

Preparation of Fatty Acid-Linker Construct #4
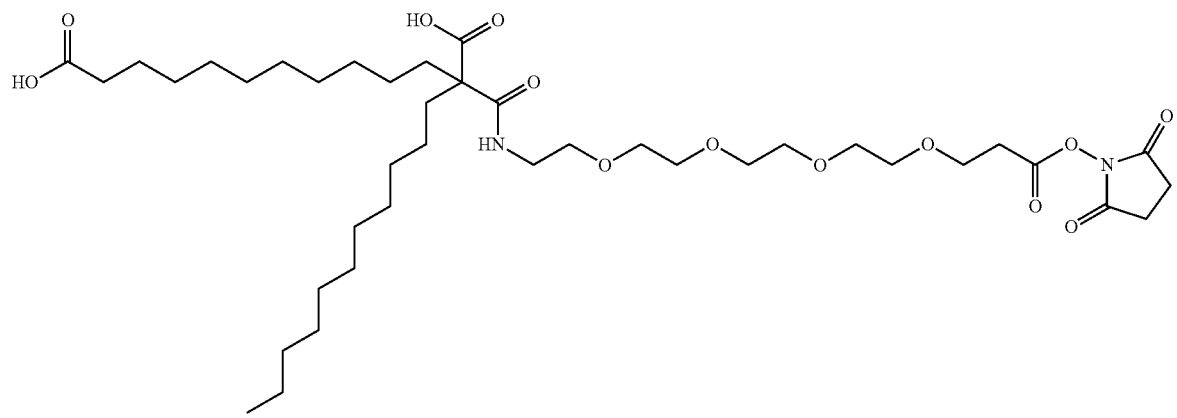 [SMILES: CCCCCCCCCCCC(CCCCCCCCCCC(=O)O)(C(=O)O)C(=O)NCCOCCOCCOCCOCCC(=O)ON1C(=O)CCC1=O]
The fatty acid-linker construct was prepared using amino-PEG4-Carboxylic acid and was isolated as a pale yellow oil;
LCMS: Method A: CAD: Rt 1.66 mins MS m/z 787.6 [M+H]+;
1H NMR (400 MHz, CDCl3): δ 7.24 (1H, br t), 3.85 (2H, t), 3.71-3.57 (14H, br m), 3.56-3.48 (2H, br m), 2.90 (2H, t), 2.84 (4H, br s), 2.35 (2H, t), 2.10-1.99 (2H, br m), 1.74-1.58 (4H, br m), 1.38-1.18 (32H, br m), 0.88 (3H, t).
Preparation of H2N-Q(Trt)-R(Pbf)-P-R(Pbf)-L-C(Trt)-H(Trt)-K(Boc)-G-P-(Nle)-C(Trt)-F-COOH
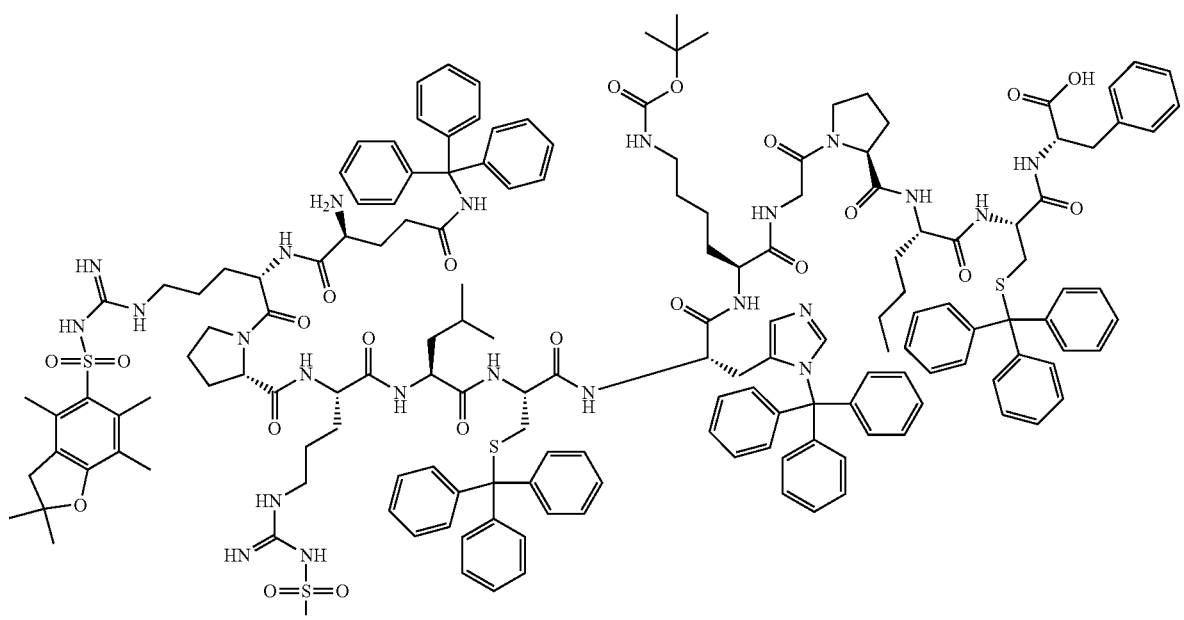

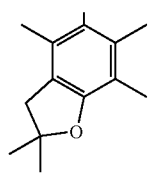

H-Phe-2-ClTrt resin

↓ SPPS

H2N—Q(Trt)—R(Pbf)—P—R(Pbf)—L—C(Trt)—H(Trt)—K(Boc)—G—P—(Nle)—C(Trt)—F—COO-2-ClTrt resin (1a)

↓ Cleavage with 20% HFIP/DCM

H2N—Q(Trt)—R(Pbf)—P—R(Pbf)—L—C(Trt)—H(Trt)—K(Boc)—G—P—(Nle)—C(Trt)—F—COOH (1b)

Step 1: Preparation of Intermediate 1a

Three batches of H-Phe-2-ClTrt resin (Novabiochem, 324 mg, 0.25 mmol, 0.73 mmol/g) was subjected to solid phase peptide synthesis on an automatic peptide synthesizer (LIBERTY BLUE) with conventional double Arg for the Arg residues. Amino acids were prepared as 0.2 M solutions in DMF.

A coupling cycle was defined as follows:

Amino acid coupling: AA (4.0 eq.), HATU (4.0 eq.), DIEA (25 eq.)

Washing: DMF (3×7 mL, 1 min each time).

Fmoc deprotection: Piperidine/DMF (1:4) (7 mL, 75° C. for 3 min).

Washing: DMF (3×7 mL, 1 min each time).

| Coupling | AA | Number of couplings × Reaction time | Reaction Temperature |
|---|---|---|---|
| 1 | Fmoc-L-Cys(Trt)-OH | 1 × 6 min | 50° C. |
| 2 | Fmoc-L-Nle-OH | 1 × 5 min | 75° C. |
| 3 | Fmoc-L-Pro-OH | 1 × 5 min | 75° C. |
| 4 | Fmoc-Gly-OH | 1 × 5 min | 75° C. |
| 5 | Fmoc-L-Lys(Boc)-OH | 1 × 5 min | 75° C. |
| 6 | Fmoc-L-His(Trt)-OH | 1 × 6 min | 50° C. |
| 7 | Fmoc-L-Cys(Trt)-OH | 1 × 6 min | 50° C. |
| 8 | Fmoc-L-Leu-OH | 1 × 5 min | 75° C. |
| 9 | Fmoc-L-Arg(Pbf)-OH | 2 × 25 min | 25° C. |
| 10 | Fmoc-L-Pro-OH | 1 × 5 min | 75° C. |
| 11 | Fmoc-L-Arg(Pbf)-OH | 2 × 25 min | 25° C. |
| 12 | Fmoc-L-Gln(Trt)-OH | 1 × 5 min | 75° C. |

After the assembly of the peptide, the resin was washed with DMF (3×10 mL), DCM (3×10 mL). The peptide resin was dried under vacuum at room temperature to give Intermediate 1a (2.347 g, 0.75 mmol).

Step 2: Preparation of Intermediate 1b, H2N-Q(Trt)-R(Pbf)-P-R(Pbf)-L-C(Trt)-H(Trt)-K(Boc)-G-P-(Nle)-C(Trt)-F-COOH To intermediate 1a (2.347 g, 0.75 mmol) was added 24 mL solution of 20% HFIP/DCM, the resulting mixture was shaked at room temperature for 20 min, then filtered, the filtered was washed with DCM (3×10 mL). The above procedure was performed for 4 times in order to get total cleavage. The combined filtrate was concentrated under vacuum to give crude intermediate 1b (2.09 g, 68%), which was directly put for next step reaction without purification. LC/MS Method E: Retention time: 1.74 mins; MS M/2+1: observed: 1565.9, calculated: 1564.458.

Example 1

Fatty Acid-Linker#1Q-R-P-R-L-C*-H-K-G-P-(Nle)-C*-F ($C_6$-$C_{12}$ Disulfide Bridge)

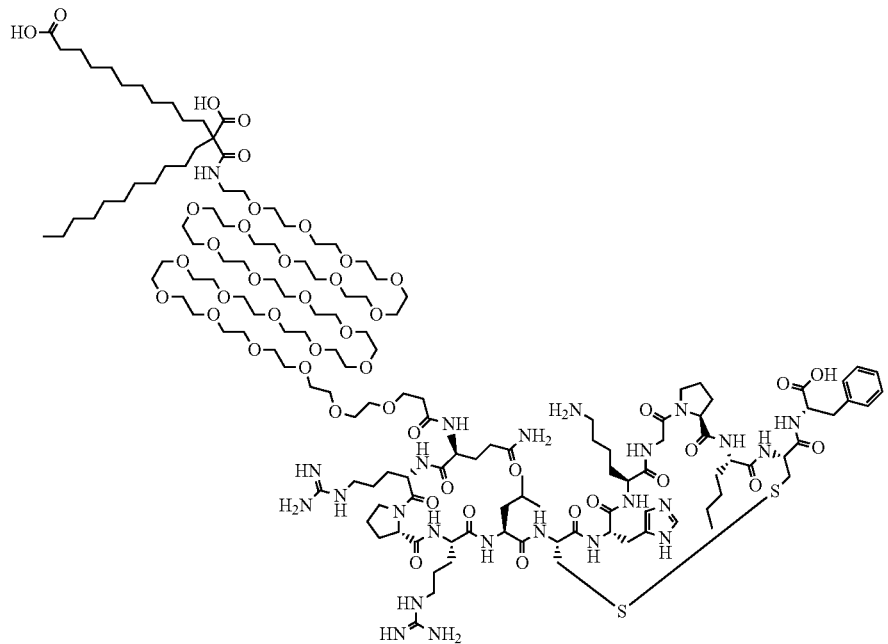 [SMILES: CCCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCOCCC(=O)N[C@@H](CCC(N)=O)C(=O)N[C@@H](CCCNC(=N)N)C(=O)N1CCC[C@H]1C(=O)N[C@@H](CCCNC(=N)N)C(=O)N[C@@H](CC(C)C)C(=O)N[C@H]1CSSC[C@@H](C(=O)N[C@@H](Cc2ccccc2)C(=O)O)NC(=O)[C@H](CCCC)NC(=O)[C@@H]2CCCN2C(=O)CNC(=O)[C@H](CCCCN)NC(=O)[C@H](Cc2cnc[nH]2)NC1=O]

Step 1

To a solution of intermediate 1b (300 mg, 0.096 mmol) in THF (100 mL) was added fatty acid-linker construct #1 (960 mg, 0.575 mmol) in THF (35 mL) and water (15 mL). The reaction mixture was stirred at room temperature. Upon completion reaction was concentrated under partial vacuum and taken through to the next reaction step as crude, assuming a quantitative yield. (Product MW: 4681.870)

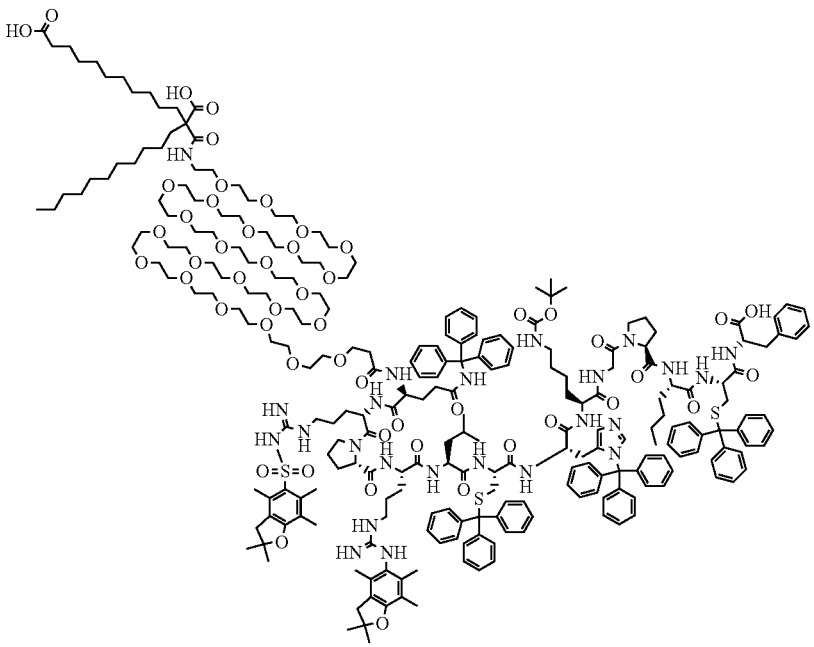

Step 2: Deprotection

To a solution of TFA (4.75 mL), TIPS (0.125 mL) and water (0.125 mL) was added DTT (296 mg, 1.920 mmol). Pre-mixed cocktail was then added to compound of step 1: (449 mg, 0.096 mmol) and stirred at room temperature. Upon completion, the reaction was concentrated under partial vacuum. The residue was treated with cooled diethyl ether, giving a cloudy reaction mixture, which was left to stand at room temperature. The resultant gum formed was isolated by decanting off the diethyl ether and rinsing with further cooled diethyl ether. The gum was dissolved in water (minimal) and loaded onto a 55 g C-18 column for reverse phase chromatography. Using a solvent gradient from 100% Water (0.1% TFA) to 100% ACN over a 20 minute period, purification afforded the deprotected compound, as a pale yellow oil (160 mg, 54% yield);

LCMS: Method D: ELSD: Rt 2.62 mins MS m/z 1555.2 [(M/2)+1-1]+;

Step 3: Cyclization-Disulfide Bond Formation

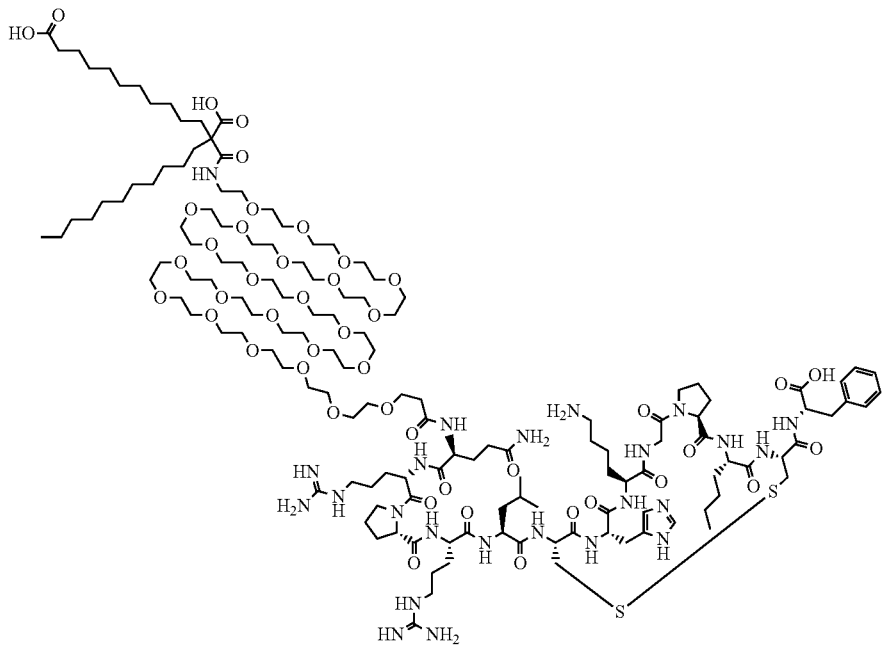 [SMILES: CCCCCCCCCCCC(CCCCCCCCCCC(=O)O)(C(=O)O)C(=O)NCCOCCOCCOCCOCCOCCOCCOCCOCCOCCOCCOCCOCCOCCOCCOCCOCCOCCOCCOCCOCCOCCOCCOCCOCCC(=O)N[C@@H](CCC(N)=O)C(=O)N[C@@H](CCCNC(=N)N)C(=O)N1CCC[C@H]1C(=O)N[C@@H](CCCNC(=N)N)C(=O)N[C@@H](CC(C)C)C(=O)N[C@H]1CSSC[C@@H](C(=O)N[C@@H](Cc2ccccc2)C(=O)O)NC(=O)[C@H](CCCC)NC(=O)[C@@H]2CCCN2C(=O)CNC(=O)[C@H](CCCCN)NC(=O)[C@H](Cc2cnc[nH]2)NC1=O]

To a solution of deprotected compound of step 2 (160 mg, 0.051 mmol) in water (2 mL) was added iodine (50 mM in AcOH) (1.339 mL, 0.067 mmol). Reaction mixture was stirred at room temperature. Upon completion the reaction mixture was loaded directly onto a 55 g C18 (55 ug) column for reverse phase chromatography. Using a solvent gradient from 100% Water (0.1% TFA) to 100% ACN over a 15 minute period the appropriate fractions by LCMS were combined and the solvent evaporated off. The resultant residue was lyophilized to afford the titled compound (Example 1) as a white solid;

LCMS: Method D: ELSD: Rt 2.64 mins; MS m/z 1554.3 [(M/2)+H]+;

The following examples were prepared analogously to Example 1 by replacing fatty acid-linker construct #1 with the appropriate fatty acid-linker constructs #2 to #4.

Example 2
Conjugate with Fatty Acid-Linker Construct #2
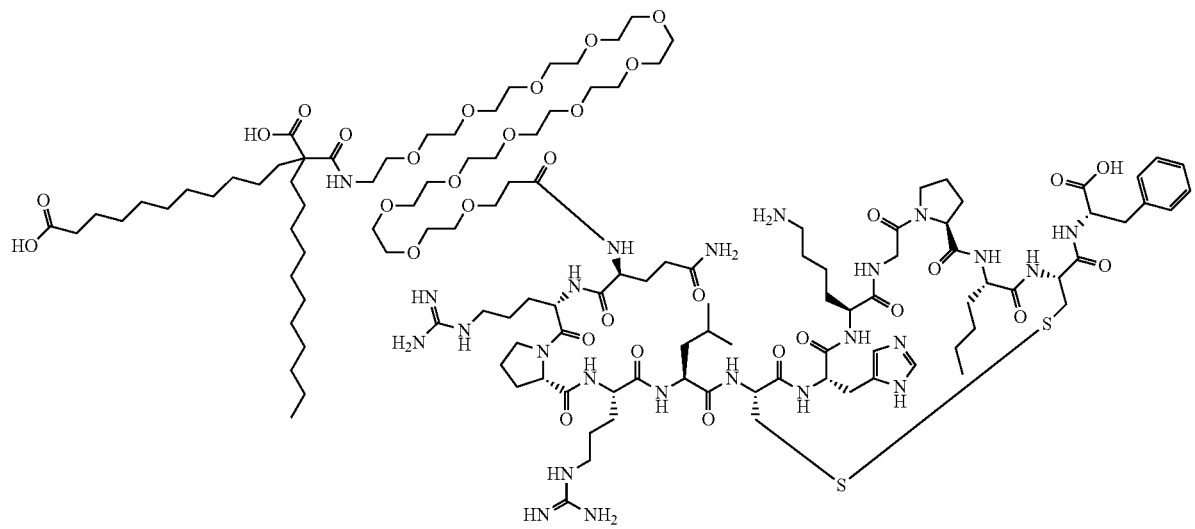 [SMILES: CCCCCCCCCCCC(CCCCCCCCCCC(=O)O)(C(=O)O)C(=O)NCCOCCOCCOCCOCCOCCOCCOCCOCCOCCOCCOCCOCCC(=O)N[C@@H](CCC(N)=O)C(=O)N[C@@H](CCCNC(=N)N)C(=O)N1CCC[C@H]1C(=O)N[C@@H](CCCNC(=N)N)C(=O)N[C@@H](CC(C)C)C(=O)N[C@H]1CSSC[C@@H](C(=O)N[C@@H](Cc2ccccc2)C(=O)O)NC(=O)[C@H](CCCC)NC(=O)[C@@H]2CCCN2C(=O)CNC(=O)[C@H](CCCCN)NC(=O)[C@H](Cc2cnc[nH]2)NC1=O]
LCMS: Method D: ELSD: Rt 2.56 mins; MS m/z 1289.9 [(M/2)+H]+;
Example 3
Conjugate with Fatty Acid-Linker Construct #3
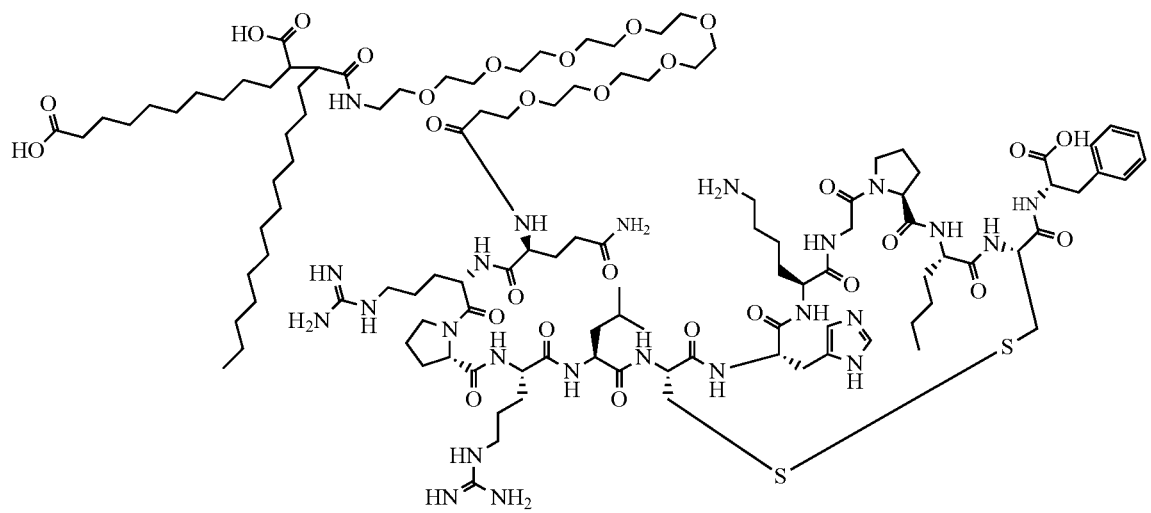 [SMILES: CCCCCCCCCCCCCC(C(=O)NCCOCCOCCOCCOCCOCCOCCOCCOCCC(=O)N[C@@H](CCC(N)=O)C(=O)N[C@@H](CCCNC(=N)N)C(=O)N1CCC[C@H]1C(=O)N[C@@H](CCCNC(=N)N)C(=O)N[C@@H](CC(C)C)C(=O)N[C@H]1CSSC[C@@H](C(=O)N[C@@H](Cc2ccccc2)C(=O)O)NC(=O)[C@H](CCCC)NC(=O)[C@@H]2CCCN2C(=O)CNC(=O)[C@H](CCCCN)NC(=O)[C@H](Cc2cnc[nH]2)NC1=O)C(CCCCCCCCCC(=O)O)C(=O)O]
LCMS: Method D: ELSD: Rt 2.52 mins; MS m/z 1201.8 [(M/2)+H]+;

Example 4

Conjugate with Fatty Acid-Linker Construct #4

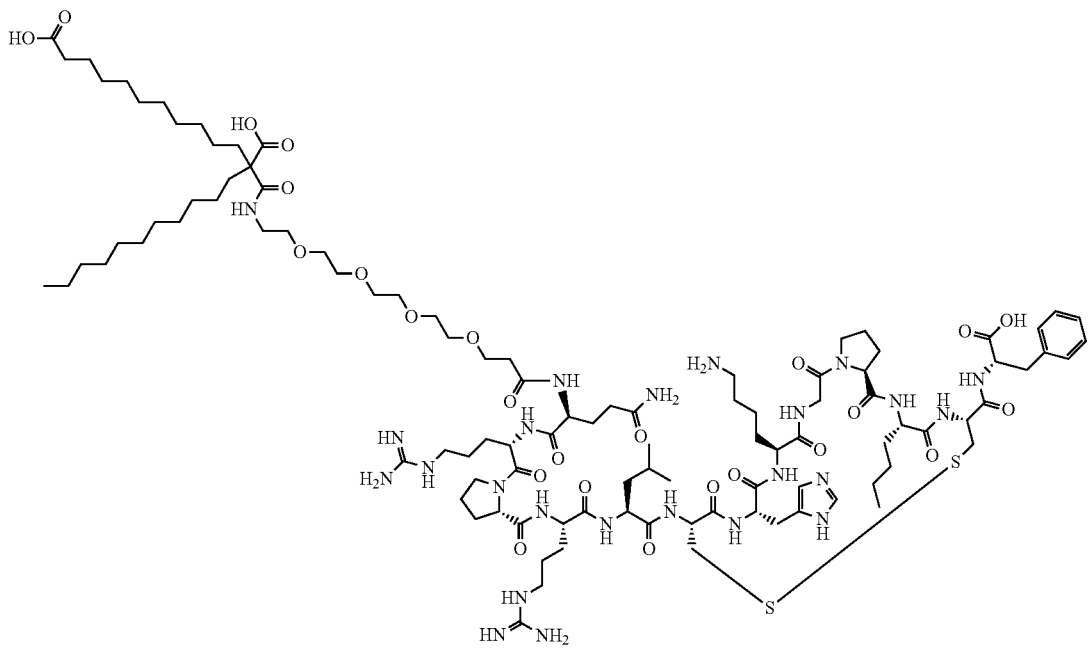 [SMILES: CCCCCCCCCCCC(CCCCCCCCCCC(=O)O)(C(=O)O)C(=O)NCCOCCOCCOCCOCCC(=O)N[C@@H](CCC(N)=O)C(=O)N[C@@H](CCCNC(=N)N)C(=O)N1CCC[C@H]1C(=O)N[C@@H](CCCNC(=N)N)C(=O)N[C@@H](CC(C)C)C(=O)N[C@H]1CSSC[C@@H](C(=O)N[C@@H](Cc2ccccc2)C(=O)O)NC(=O)[C@H](CCCC)NC(=O)[C@@H]2CCCN2C(=O)CNC(=O)[C@H](CCCCN)NC(=O)[C@H](Cc2cnc[nH]2)NC1=O]

LCMS: Method D: ELSD: Rt 2.49 mins; MS m/z 1113.6 [(M/2)+H]+;

The conjugates in the examples above have been found to have $EC_{50}$ values in the range of about 0.01 nM to about 1100 nM for APJ receptor potency. The conjugate in the examples above have been found to have a plasma stability higher than 30 minutes, higher than 60 minutes, higher than 5 h, higher than 10 h, higher than 12 h.

It can be seen that the conjugates of the invention are useful as agonist of the APJ receptor and therefore useful in the treatment of diseases and conditions responsive the activation of the APJ receptor, such as the diseases disclosed herein.

Having thus described exemplary embodiments of the present invention, it should be noted by those of ordinary skill in the art that the within disclosures are exemplary only and that various other alternatives, adaptations, and modifications may be made within the scope of the present invention. Accordingly, the present invention is not limited to the specific embodiments as illustrated therein.

What is claimed is:

1. A conjugate, or a pharmaceutically acceptable salt thereof, comprising:

a. An APJ agonist peptide having the following formula (I):

Q-R-P-R-L-C*-H-K-G-P-(Nle)-C*-F    (I), or an amide or ester thereof; wherein the two cysteine amino acids labeled with "*" form a disulfide bond between the thiol functionalities of their side chain; and b. a fatty acid selected from:

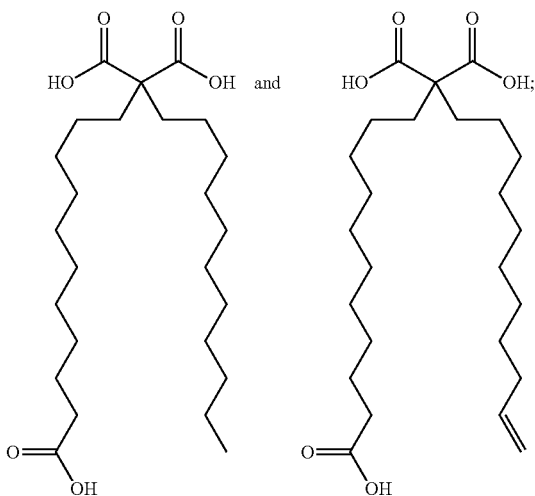 [SMILES: CCCCCCCCCCCC(CCCCCCCCCCC(=O)O)(C(=O)O)C(=O)O ; C=CCCCCCCCCCC(CCCCCCCCCCC(=O)O)(C(=O)O)C(=O)O]

wherein said fatty acid is covalently linked to the N-terminus of the peptide via one of its carboxylic acid functionality, and via a polyethylene glycol linker of Formula (III):

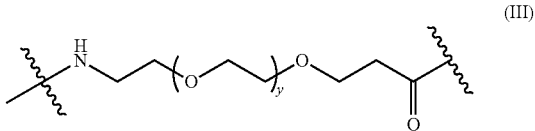

(III) wherein y is 1-30, wherein the carbonyl functionality of the PEG linker forms an amide bond with the amino functionality at the N-terminus of the peptide of Formula (I) and wherein the amino functionality of the PEG linker forms an amide bond with one of the carboxylic acid functionalities of the fatty acid.

2. The conjugate according to claim 1 wherein the polyethylene glycol linker is of Formula (III) and y is 2 to 25.

3. The conjugate according to claim 1 wherein the fatty acid is

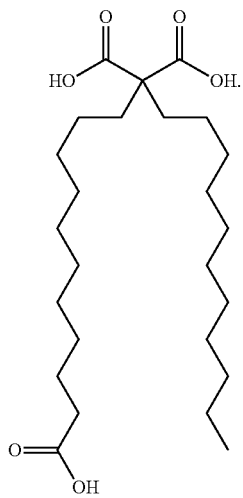 [SMILES: CCCCCCCCCCCC(CCCCCCCCCCC(=O)O)(C(=O)O)C(=O)O]

4. The conjugate according to claim 1 wherein the fatty acid is attached to the amino functionality of the PEG linker via one of its geminal carboxylic acid functionality.

5. The conjugate according to claim 1 wherein the fatty acid is attached to the amino functionality of the PEG linker via its terminal carboxylic acid functionality.

6. A conjugate selected from:

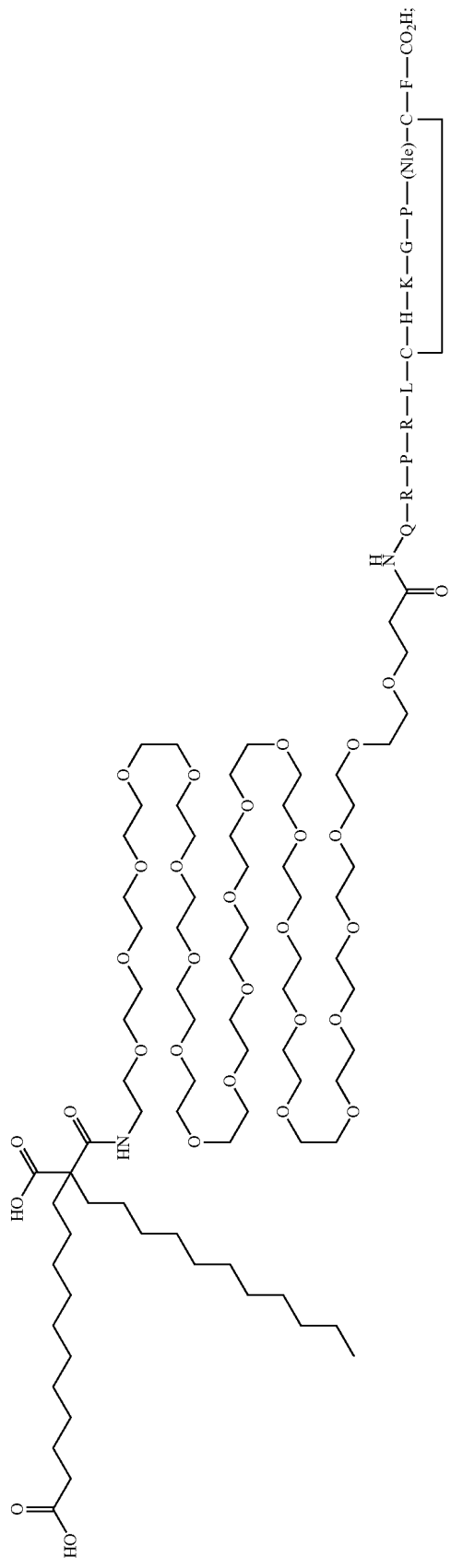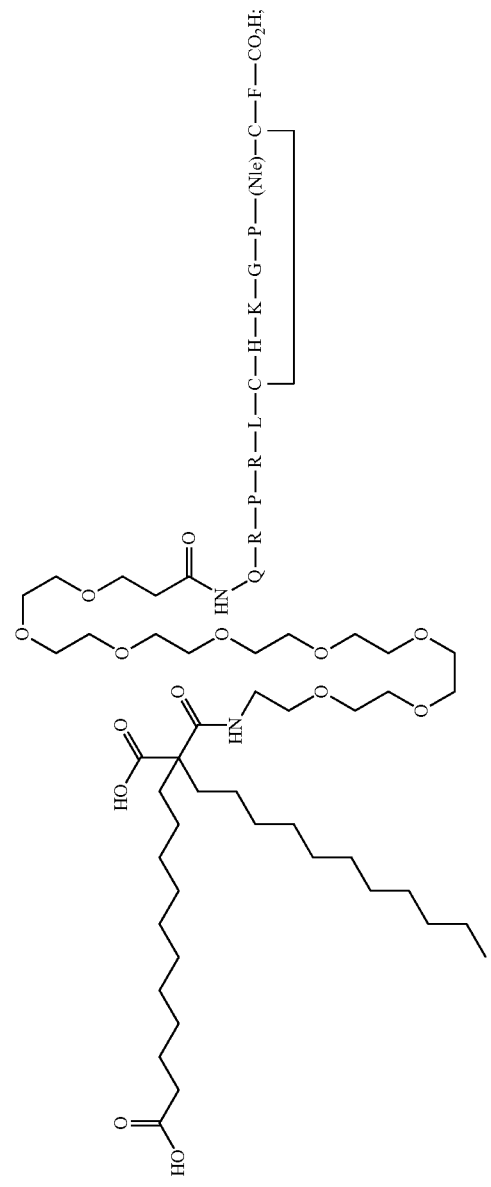

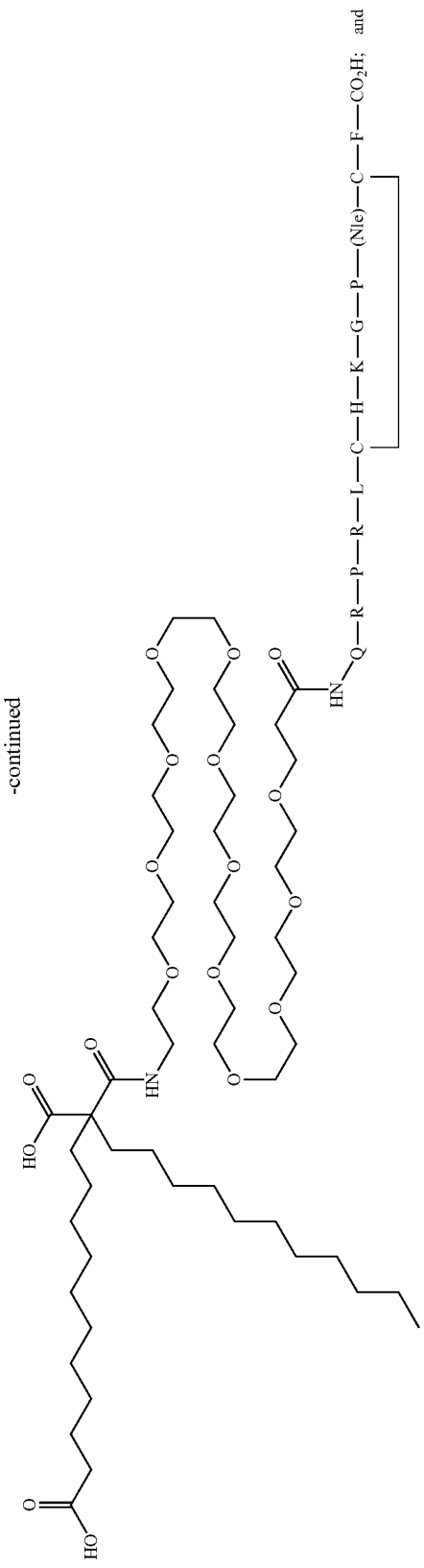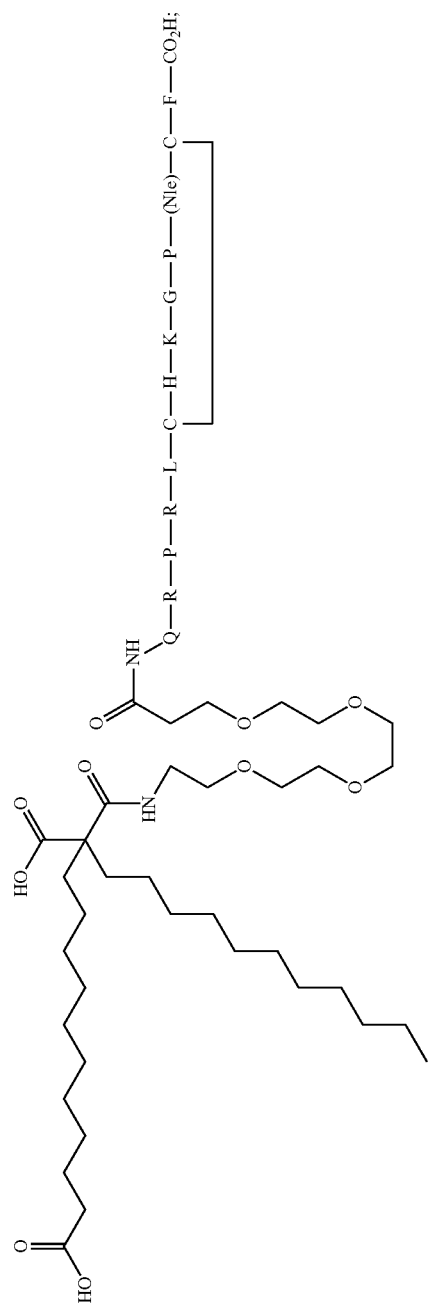

or a pharmaceutically acceptable salt thereof.

7. A method of treating or preventing a disease or disorder responsive to the agonism of the APJ receptor, in a subject in need thereof, comprising administering to the subject a therapeutically effective amount of a conjugate according to claim 1; or a pharmaceutically acceptable salt thereof.

8. The method of claim 7 wherein the disease or disorder is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

9. A combination comprising a therapeutically effective amount of a conjugate according to claim 1 or a pharmaceutically acceptable salt thereof, and one or more therapeutically active co-agents.

10. A combination according to claim 9 wherein the co-agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

11. A pharmaceutical composition comprising a therapeutically effective amount of a conjugate according to claim 1 or a pharmaceutically acceptable salt thereof, and one or more pharmaceutically acceptable carriers.

12. A method of treating a disease or disorder responsive to the agonism of the APJ receptor, in a subject in need thereof, comprising administering to the subject a therapeutically effective amount of a conjugate according to claim 6; or a pharmaceutically acceptable salt thereof.

13. The method of claim 12 wherein the disease or disorder is selected from acute decompensated heart failure (ADHF), chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes (including gestational diabetes), obesity, peripheral arterial disease, cerebrovascular accidents, transient ischemic attacks, traumatic brain injuries, amyotrophic lateral sclerosis, burn injuries (including sunburn) and preeclampsia.

14. A combination comprising a therapeutically effective amount of a conjugate according to claim 6, or a pharmaceutically acceptable salt thereof, and one or more therapeutically active co-agents.

15. A combination according to claim 14 wherein the co-agent is selected from inotropes, beta adrenergic receptor blockers, HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), a CETP inhibitor, anti-coagulants, relaxin, BNP (nesiritide) and a NEP inhibitor.

16. A pharmaceutical composition comprising a therapeutically effective amount of a conjugate according to claim 6, or a pharmaceutically acceptable salt thereof, and one or more pharmaceutically acceptable carriers.

\* \* \* \* \*

UNITED STATES PATENT AND TRADEMARK OFFICE
CERTIFICATE OF CORRECTION

PATENT NO. : 9,931,372 B2
APPLICATION NO. : 14/996418
DATED : April 3, 2018
INVENTOR(S) : Kanter et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 122 days.

Signed and Sealed this
Fifth Day of February, 2019

Andrei Iancu
*Director of the United States Patent and Trademark Office*